US008404880B2

(12) United States Patent
Kaji et al.

(10) Patent No.: US 8,404,880 B2
(45) Date of Patent: Mar. 26, 2013

(54) SOLID POLYMETHYLALUMINOXANE COMPOSITION AND METHOD FOR MANUFACTURING SAME

(75) Inventors: Eiichi Kaji, Shunan (JP); Etsuo Yoshioka, Shunan (JP)

(73) Assignee: Tosoh Finechem Corporation, Shunan-Shi (JP)

( * ) Notice: Subject to any disclaimer, the term of this patent is extended or adjusted under 35 U.S.C. 154(b) by 0 days.

(21) Appl. No.: 13/128,632

(22) PCT Filed: Nov. 11, 2009

(86) PCT No.: PCT/JP2009/006019
§ 371 (c)(1),
(2), (4) Date: Jul. 28, 2011

(87) PCT Pub. No.: WO2010/055652
PCT Pub. Date: May 20, 2010

(65) Prior Publication Data
US 2011/0282017 A1 Nov. 17, 2011

(30) Foreign Application Priority Data
Nov. 11, 2008 (JP) .................................. 2008-289211

(51) Int. Cl.
*C07F 5/06* (2006.01)
*C08F 4/642* (2006.01)
*C08F 4/6592* (2006.01)

(52) U.S. Cl. ........ 556/179; 502/103; 502/152; 526/160; 526/165; 526/943; 556/182

(58) Field of Classification Search .................. 556/179, 556/182; 502/103, 152; 526/160, 165, 943
See application file for complete search history.

(56) References Cited

U.S. PATENT DOCUMENTS

| | | | |
|---|---|---|---|
| 4,536,484 | A | 8/1985 | Lacombe et al. |
| 4,542,199 | A | 9/1985 | Kaminsky et al. |
| 4,952,540 | A | 8/1990 | Kioka et al. |
| 5,070,160 | A | 12/1991 | Tomotsu et al. |
| 5,728,855 | A | 3/1998 | Smith et al. |
| 5,777,143 | A | 7/1998 | Malpass et al. |
| 5,831,109 | A | 11/1998 | Smith et al. |
| 2007/0197745 | A1 | 8/2007 | Kaji et al. |

FOREIGN PATENT DOCUMENTS

| | | |
|---|---|---|
| CN | 88101337 | 12/1988 |
| EP | 0279586 | 8/1988 |
| EP | 0399384 | 11/1990 |
| EP | 0906914 | 4/1999 |
| EP | 1728795 | 12/2006 |
| JP | 58-19309 | 2/1983 |
| JP | 63-35005 | 2/1985 |
| JP | 60-260602 | 12/1985 |
| JP | 62-234009 | 10/1987 |
| JP | 63-89506 | 4/1988 |
| JP | 63-178108 | 7/1988 |
| JP | 07-42301 B2 | 8/1988 |
| JP | 63-198691 | 8/1988 |
| JP | 63-234009 | 9/1988 |
| JP | 64-66214 | 3/1989 |
| JP | 01-207355 | 8/1989 |
| JP | 01-315407 | 12/1989 |
| JP | 02-22308 | 1/1990 |
| JP | 02-308802 | 12/1990 |
| JP | 07-70144 | 3/1995 |
| JP | 07-300486 | 11/1995 |
| JP | 08-319309 | 12/1996 |
| JP | 2000-95810 | 4/2000 |
| JP | 2000-505785 | 5/2000 |
| JP | 2001-502714 | 2/2001 |
| JP | 2005-263749 | 9/2005 |
| WO | WO 97/23288 | 7/1997 |

OTHER PUBLICATIONS

English translation of the International Preliminary Report on Patentability (Chapter I) for International Application No. PCT/JP2009/006019.
International Search Report for International Application No. PCT/JP2009/006019, Jan. 19, 2010.
Written Opinion of the International Searching Authority for International Application No. PCT/JP2009/006019, Jan. 19, 2010.
Chinese Office Action for corresponding CN Application No. 200980144954.7, Aug. 10, 2012.
Singapore Office Action for corresponding Singapore Application No. 201103338-8, Aug. 6, 2012.

*Primary Examiner* — Caixia Lu
(74) *Attorney, Agent, or Firm* — Ditthavong Mori & Steiner, P.C.

(57) ABSTRACT

Disclosed are: a solid polymethylaluminoxane composition which does not utilize silica or the like, has the form of relatively fine particles, has more uniform particle sizes, and exhibits a high polymerization activity when used in the preparation of an olefin polymer; a process for producing the solid polymethylaluminoxane composition; a polymerization catalyst; and a process for producing an olefin polymer. Specifically disclosed are: a solid polymethylaluminoxane composition which has an aluminum content of 36 to 41 mass % and contains a methyl group derived from a trimethylaluminum moiety at a molar fraction of 12 mol % or less; a process for producing the solid polymethylaluminoxane composition, which comprises the step of heating an aromatic hydrocarbon solution containing polymethylaluminoxane and trimethylaluminum to cause the precipitation of the solid polymethylaluminoxane composition; a polymerization catalyst for an olefin, which comprises the solid polymethylaluminoxane composition and a transition metal compound as catalyst components; and a process for producing an olefin polymer by using the polymerization catalyst.

17 Claims, 5 Drawing Sheets

SOLID POLYMETHYLALUMINOXANE COMPOSITION AND METHOD FOR MANUFACTURING SAME

CROSS-REFERENCE TO RELATED PATENT APPLICATION

The present application claims priority under Japanese Patent Application 2008-289211, filed on Nov. 11, 2008, the entire contents of which are hereby incorporated by reference.

TECHNICAL FIELD

The present invention relates to a solid polymethylaluminoxane composition employed in the polymerization of olefins, to a method for manufacturing the same, to a polymerization catalyst employing the solid polymethylaluminoxane composition as a catalytic component, and to a method for manufacturing the same.

BACKGROUND ART

Polyaluminoxane compositions in solution are condensation products generally prepared by partial hydrolysis of organic aluminum compounds. They are known to be useful as promoter (co-catalytic) components that efficiently activate transition metal compounds serving as primary catalysts in the manufacturing of olefin polymers. Polymethylaluminoxane compositions in which trimethylaluminum is employed as a starting material organic aluminum compound are widely known to exhibit particularly good performance as promoters. These compositions can usually be handled in solution form when dissolved in an aromatic hydrocarbon solvent such as toluene (see Patent References 1 to 6 and the like).

Polymethylaluminoxane compositions exhibit good promoter's performance. However, they are normally handled in a state in which a polymethylaluminoxane composition is dissolved in a solvent with a primary catalyst such as a metallocene compound, and the morphology of the polymer produced cannot be controlled. Thus, not only does handling of the polymer become difficult, but there is a problem in that fouling due to adhesion of the polymer to the polymerization reaction vessel or the like is highly prone to occur.

To solve these problems, a method of applying a supported solid polymethylaluminoxane composition, in which a polymethylaluminoxane composition is supported on a solid inorganic support such as silica, alumina, or magnesium chloride, to suspension polymerization or vapor phase polymerization has been proposed. Among solid inorganic supports, silica with a controlled quantity of surface hydroxyl groups is the most widely employed, and there are quite a few examples of extension to the industrial level (see Patent References 7 to 11, 17, and the like).

The silica support tends to remain in the polymer and is known to compromise the performance of the polymer. Further, solid polymethylaluminoxane compositions in which such a support is employed are known to exhibit much lower activity than the polymerization activity in homogeneous polymerization. Accordingly, to solve these problems, the development of a solid polymethylaluminoxane composition having high activity rivaling that of homogeneous polymerization while retaining the advantages of a promoter in the form of a solid polymethylaluminoxane composition has been eagerly awaited.

Attempts have been made to obtain a solid polymethylaluminoxane composition without using a solid support such as that set forth above. Generally, when attempting to prepare a solid polymethylaluminoxane composition, the method of reacting some additive with a liquid polymethylaluminoxane composition is adopted (see Patent References 12 to 16 and the like). However, in such methods, the recovery rate of the solid material based on aluminum is not high.

Patent Reference 1: JP-A-S58(1983)-19309
Patent Reference 2: JP-A-S60(1985)-35005
Patent Reference 3: JP-A-S62(1987)-234009
Patent Reference 4: JP-A-S63(1988)-234009
Patent Reference 5: JP-A-S64(1989)-66214
Patent Reference 6: JP-A-H01(1989)-207355
Patent Reference 7: JP-A-S60(1985)-260602
Patent Reference 8: JP-A-S63(1988)-89506
Patent Reference 9: JP-A-S63(1988)-178108
Patent Reference 10: JP-A-H01(1989)-315407
Patent Reference 11: JP-A-H02(1990)-22308
Patent Reference 12: JP-A-2000-95810
Patent Reference 13: JP-A-H08(1996)-319309
Patent Reference 14: JP-A-H07(1995)-300486
Patent Reference 15: JP-A-H07(1995)-70144
Patent Reference 16: JP-A-H07(1995)-42301
Patent Reference 17: JP-A-2000-505785(WO97/23288)

The disclosures of Patent References 1 to 17 are expressly incorporated herein by reference in their entirety.

SUMMARY OF THE INVENTION

Problem to be Solved by the Invention

It is better to avoid the addition of a third component to obtain a solid polymethylaluminoxane composition because there are cases in which it causes problems such as toxicity in some applications of polymers. Based on such considerations, methods of obtaining a solid polymethylaluminoxane composition by adding just a solvent of little or no solubility to a liquid polymethylaluminoxane composition have been proposed. Patent References 12 and 16 propose methods of adding n-hexane or n-decane at room temperature to a toluene solution of a polymethylaluminoxane composition to cause precipitation of a solid polymethylaluminoxane composition, and then removing the solvent with a vacuum pump to increase the amount of precipitation.

The methods described in Patent References 12 and 16 give the yields and average particle diameters of the solid polymethylaluminoxane compositions that precipitate, but provide no other details relating to morphology.

When preparing an olefin polymer by combining a solid polymethylaluminoxane composition with a transition metal compound, the morphology of the solid polymethylaluminoxane composition greatly affects the properties of the olefin polymer that is prepared. Generally, solid polymethylaluminoxane compositions are microparticles, and the more uniform the particle diameter, the more uniform the particles of the olefin polymer that is prepared, which is desirable. The particle diameters of the solid polymethylaluminoxane compositions described in the embodiments of Patent Reference 12 are 210 to 350 μm, and the particle diameters of the solid polymethylaluminoxane compositions described in Patent Reference 16 are 28 to 47 μm. That is, in these patent references, the description is unclear as to how it might be possible to prepare a solid polymethylaluminoxane composition with a particle diameter of 30 μm or less, and the description in the embodiments is unclear as to the degree of homogeneity of particle diameter of the solid polymethylaluminoxane compositions.

Solid polymethylaluminoxane compositions generally also present a problem in the form of lower polymerization activity than liquid polymethylaluminoxane compositions. Further, as regards the yields of solid polymethylaluminoxane compositions, the entire quantity of polymethylaluminoxane contained in a liquid polymethylaluminoxane composition is not recovered as a solid polymethylaluminoxane composition. The lower the yield, the higher the cost. In the course of obtaining a solid polymethylaluminoxane composition as is done by the methods described in Patent References 12 and 16, the method of removing a large quantity of solvent from the liquid polymethylaluminoxane composition by means of a vacuum pump can be implemented without any particular problems at the laboratory level. However, consideration of implementation on a commercial scale reveals the possibility of scattering trimethylaluminum, which is never solid, and polymethylaluminoxane to the vacuum pump side. Not only is this dangerous, but it presents numerous problems from the perspective of productivity, rendering this formula impractical.

Accordingly, the problem to be solved by the present invention is to provide a solid polymethylaluminoxane composition comprised of relatively minute particles—with, for example, a median diameter based on volume falling within a range of 5 to 50 µm—and having a more uniform particle diameter, without employing a solid support such as silica or a third component. A further problem to be solved is how to provide a solid polymethylaluminoxane composition that is comprised not just of relatively minute particles of more uniform particle diameter, but which also has high polymerization activity when preparing olefin polymers, desirably having activity rivaling that of liquid polymethylaluminoxane compositions.

A further problem to be solved by the present invention is to provide a method in which the yield of polymethylaluminoxane composition is high in the preparation of a solid polymethylaluminoxane composition from a liquid polymethylaluminoxane composition, and that does not require the removal of solvent by means of a vacuum pump from the liquid polymethylaluminoxane composition.

A still further problem to be solved by the present invention is how to provide a method for inexpensively manufacturing with industrial efficiency a quality olefin polymer using the above solid polymethylaluminoxane composition and a transition metal compound.

Means of Solving the Problems

The present invention is as set forth below.

[1]
A solid polymethylaluminoxane composition wherein:
(i) the aluminum content falls within a range of 36 mass % to 41 mass %;
(ii) the mole fraction of methyl groups derived from the trimethylaluminum component relative to the total number of moles of methyl groups is 12 mol % or lower.

[2]
The composition according to [1], having a particulate form with a volume-based median diameter falling within a range of 5 to 50 µm.

[3]
The composition according to [1] or [2], having a solubility in n-hexane at 25° C. of 0 to 2 mol %, and having a solubility in toluene at 25° C. of 0 to 2 mol %.

[4]
The composition according to any one of [1] to [3], wherein the homogeneity denoted by the following equation is 0.45 or lower:

$$\text{Homogeneity} = \Sigma(\text{SIGMA})Xi|d(0.5)-Di|/d(0.5)\Sigma(\text{SIGMA})Xi$$

(wherein Xi denotes the histogram value of a particle i, d(0.5) denotes the median diameter based on volume, and Di denotes the diameter based on volume of particle i).

[5]
The composition according to any one of [1] to [4], having a specific surface area falling within a range of 10 to 25 $m^2$/mmol-Al.

[6]
The composition according to any one of [1] to [5], comprising polymethylaluminoxane containing the unit denoted by general formula (I) below and trimethylaluminum:

$$-[(\text{Me})\text{AlO}]_n- \quad (I)$$

(wherein n denotes an integer of from 10 to 50).

[7]
The composition according to any one of [1] to [6], containing no $SiO_2$.

[8]
A method for manufacturing the solid polymethylaluminoxane composition described in any one of [1] to [7], comprising the step of:

(a) heating an aromatic hydrocarbon solution containing polymethylaluminoxane containing the unit denoted by general formula (II) below and trimethylaluminum (referred to as the "polymethylaluminoxane composition in solution" hereinafter) to precipitate a solid polymethylaluminoxane composition containing polymethylaluminoxane and trimethylaluminum:

$$-[(\text{Me})\text{AlO}]_n- \quad (II)$$

(wherein n denotes an integer of from 1 to 50).

[9]
The manufacturing method according to [8], wherein the polymethylaluminoxane composition in solution prior to heating exhibits 15 mol % or less of a mole fraction of methyl groups derived from the trimethylaluminum component relative to the total number of moles of methyl groups.

[10]
The manufacturing method according to [8] or [9], wherein in step (a), a heating temperature and a heating time suited to precipitating the solid polymethylaluminoxane composition are selected from:
(i) a heating temperature ranging from 80 to 200° C.; and
(ii) a heating time of 5 minutes or more but less than 24 hours.

[11]
The manufacturing method according to any one of [8] to [10], wherein the polymethylaluminoxane composition in solution that is employed as a starting material in step (a) is obtained by thermally decomposing an alkylaluminum compound having an aluminum-oxygen-carbon bond.

[12]
The manufacturing method according to [11], wherein the alkyl aluminum compound having an aluminum-oxygen-carbon bond is prepared by reacting trimethylaluminum and an oxygen-containing organic compound.

[13]
The manufacturing method according to [12], wherein the oxygen-containing organic compound is the aliphatic or aromatic carboxylic acid denoted by general formula (III):

$$R^1-(\text{COOH})_n \quad (III)$$

(wherein $R^1$ denotes a hydrocarbon group in the form of a C1 to C20 linear or branched alkyl group, alkenyl group, or aryl group, and n denotes an integer of 1 to 5).

[14]
An olefin polymerization catalyst containing catalytic components in the form of the solid polymethylaluminoxane composition according to any one of [1] to [7] and a transition metal compound denoted by general formula (IV) below:

$$MR^5R^6R^7R^8 \qquad (IV)$$

(wherein M denotes a transition metal element, and $R^5$, $R^6$, $R^7$, and $R^8$, which are joined together, denote organic groups having a cycloalkadienyl skeleton, alkyl groups, alkoxy groups, aryloxy groups, alkylsilyl groups, alkylamide groups, alkylimide groups, alkylamino groups, alkylimino groups, or halogen atoms).

[15]
A method for manufacturing a polyolefin, comprising polymerizing an olefin using the catalyst according to [14].

Effect of the Invention

The present invention provides a solid polymethylaluminoxane compound in the form of relatively minute particles of uniform particle size, extremely simply and at high yield. The solid polymethylaluminoxane composition of the present invention exhibits extremely high polymerization activity when employed in polymerization as a promoter. Further, the solid polymethylaluminoxane composition of the present invention has extremely low solubility in solvents, and thus markedly suppresses fouling of the reaction vessel when employed in polymerization, yielding a polymer of uniform particle diameter.

MODES OF CARRYING OUT THE INVENTION

The Solid Polymethylaluminoxane Composition

Figure 1:
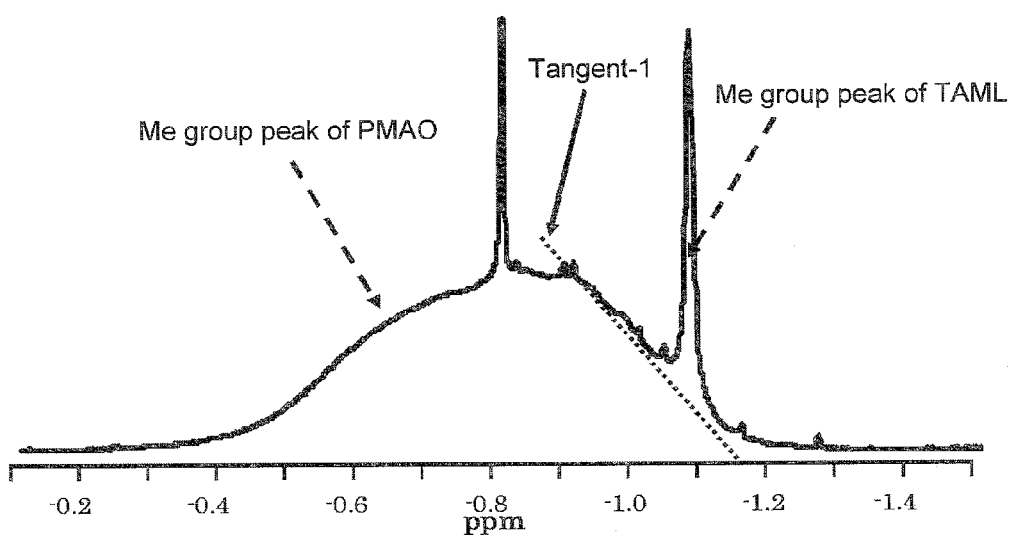
FIG. 1 A $^1$H-NMR chart of a polymethylaluminoxane composition in solution obtained based on the present invention.

In the solid polymethylaluminoxane composition of the present invention:
(i) the aluminum content falls within a range of 36 mass % to 41 mass %;
(ii) the mole fraction of methyl groups derived from the trimethylaluminum component relative to the total number of moles of methyl groups is 12 mol % or lower.

The solid polymethylaluminoxane composition of the present invention contains polymethylaluminoxane and trimethylaluminum. The state of coexistence of the polymethylaluminoxane and trimethylaluminum is not necessarily clear, but the polymethylaluminoxane and trimethylaluminum are incorporated in a compositional ratio and state of presence satisfying (i) and (ii) above.

The polymethylaluminoxane can contain the unit denoted by general formula (I) below:

$$-[(Me)AlO]_n- \qquad (I)$$

(wherein n denotes an integer of from 10 to 50).

The phrase "contains the unit denoted by general formula (I)" means that it contains polymethylaluminoxane in which n denotes a single number falling within the above range (n being a specified integer) or contains multiple polymethylaluminoxanes of multiple types (n denoting multiple different integers). The reason n denotes an integer of 10 to 50 is because the n of the polymethylaluminoxane in the polymethylaluminoxane composition in solution serving as the starting material of the solid polymethylaluminoxane composition is 10 to 50. In the literature, it is recorded that disproportionation of the polymethylaluminoxane chains in the polymethylaluminoxane composition in solution or of the polymethylaluminoxane chain and the trimethylaluminum causes change in the length of the polymethylaluminoxane chain. Trimethylaluminum is produced when there is disproportionation of the polymethylaluminoxane chains, and trimethylaluminum is consumed when there is disproportionation of the polymethylaluminoxane chain and the trimethylaluminum. However, $^1$H-NMR measurement conducted with $d_8$-THF as solvent on the solid polymethylaluminoxane before washing with solvent revealed no pronounced change in the content of trimethylaluminum. On that basis, the n of the polymethylaluminoxane in the solid polymethylaluminoxane composition was thought to be approximately equivalent to the n of the polymethylaluminoxane composition in solution that was used as a starting material. In the present invention, so long as the polymethylaluminoxane contains the above unit, it can be of a linear, cyclic, or branched structure.

When the polymethylaluminoxane is of a cyclic structure, the theoretical quantity of the aluminum content is about 46 to 47 mass % and the theoretical quantity of the aluminum content of the trimethylaluminum is about 38 mass %. That is, when the aluminum content of the solid polymethylaluminoxane composition exceeds 46 mass %, the solid polymethylaluminoxane composition is thought to be comprised of just polymethylaluminoxane of a cyclic structure, with almost no trimethylaluminum being present and with absolutely no impurities such as solvent being contained. When the polymethylaluminoxane is of a linear structure, the theoretical quantity of the aluminum content depends on the number n in general formula (I), but is smaller than when of a cyclic structure. Additionally, the solid polymethylaluminoxane composition of the present invention contains polymethylaluminoxane of a linear structure and of a branched structure in addition to polymethylaluminoxane of a cyclic structure, and impurities such as residual solvent are contained in the trimethylaluminum. Thus, in the solid polymethylaluminoxane composition of the present invention, as indicated by (i), the aluminum content falls within a range of from 36 mass % to 41 mass %. The lower the aluminum content, the greater the ratio of trimethylaluminum that is present; and the higher the aluminum content, the lower the proportion of trimethylaluminum present tends to be.

Since the aluminum content falls within a range of 36 mass % to 41 mass %, the solid polymethylaluminoxane composition has properties such as good particle diameter homogeneity and strength preventing crushing due to a tendency to split. Conversely, an aluminum content of less than 36 mass % in the present invention is indicative of inadequate drying and the excessive incorporation of impurities such as solvent. When the aluminum content exceeds 46 mass %, the presence of polymethylaluminoxane of primarily cyclic structure is presumed. It also indicates that almost no trimethylaluminum or solvent impurities have been incorporated, but the composition itself differs from the solid polymethylaluminoxane composition obtained by the present invention. From the above perspectives, the aluminum content desirably falls within a range of 38 mass % to 41 mass %.

The aluminum content of the solid aluminoxane composition and polymethylaluminoxane composition in solution that are prepared in the present invention can be determined, for example, by adding an excessive quantity of disodium ethylenediaminetetraacetate to a solution that has been hydrolyzed with 0.5 N sulfuric acid aqueous solution and then conducting reverse titration with zinc sulfate using dithizone as indicator. When the measured concentration is dilute, measurement can be conducted by atomic absorption analysis.

In the mole fraction of the methyl groups derived from the trimethylaluminum component relative to the total number of moles of methyl groups denoted by (ii), the total number of moles of methyl groups is the total of the number of moles of methyl groups derived from polymethylaluminoxane and the number of moles of methyl groups derived from trimethylaluminum. The number of moles of methyl groups derived from the trimethylaluminum component is the number of moles of methyl groups derived from trimethylaluminum. The mole fraction of the methyl groups derived from the trimethylaluminum component is 12 mol % or less. A low mole fraction of methyl groups derived from the trimethylaluminum component means that there are few methyl groups derived from the trimethylaluminum component contained in the polymethylaluminoxane, with the state where the aluminum is on a polymethylaluminoxane chain being a few. The mole fraction of methyl groups derived from the trimethylaluminum component kept at less than 12 mol % yields a solid polymethylaluminoxane composition with little solubility in solvent that has strength that prevents the particles from crumbling even during the drying process. Conversely, when the mole fraction of methyl groups derived from the trimethylaluminum component exceeds 12 mol %, the solubility in solvent increases and the particles tend to be crushed easily.

In the solid methylaluminoxane composition of the present invention, the mole fraction of methyl groups derived from the trimethylaluminum component is desirably 11 mol % or lower. The lower limit of the mole fraction of methyl groups derived from the trimethylaluminum component depends on the polymethylaluminoxane solution serving as a starting material permitting control of the shape of the solid polymethylaluminoxane and is thus, for example, 6 mol %, desirably 8 mol %.

The polymethylaluminoxane composition employed in the present invention contains internal trimethylaluminum as an unreacted starting material. In the present invention, the quantity of trimethylaluminum present in the polymethylaluminoxane composition is expressed as the mole fraction of the methyl groups derived from polymethylaluminoxane and trimethylaluminum (abbreviated as Me(PMAO) and Me(TMAL), respectively).

The mole fractions of the respective components of the polymethylaluminoxane composition can be determined from the area ratios assigned to the respective components in $^1$H-NMR measurement of the polymethylaluminoxane composition. An example of the method of determining the specific mole fractions of Me(PMAO) and Me(TMAL) of the polymethylaluminoxane composition is given in the embodiments.

The solid polymethylaluminoxane composition of the present invention is particulate. The homogeneity denoted by the equation below is desirably 0.45 or less:

$$\text{Homogeneity} = \Sigma(\text{SIGMA})Xi|d(0.5) - Di|/d(0.5)\Sigma(\text{SIGMA})Xi$$

(wherein Xi denotes the histogram value of a particle i, d(0.5) denotes the median diameter based on volume, and Di denotes the diameter based on volume of particle i).

The homogeneity of the particulate solid polymethylaluminoxane composition of the present invention kept at 0.45 or lower yields an olefin polymer of uniform particle diameter using the solid polymethylaluminoxane composition and a transition metal composition. The homogeneity is desirably 0.4 or lower, preferably 0.35 or lower, and more preferably, 0.3 or lower. The lower the value of the homogeneity, the more uniform the particle diameters of the particles of olefin polymer obtained tend to be. This homogeneity is employed as an index of catalyst particle size distribution. The greater the value of this index, the broader the distribution indicated. The lower limit of this homogeneity is, for example, 0.15 taking into account the fact that the particle shape is controlled by self-association of the solid polymethylaluminoxane composition.

Further, the solid polymethylaluminoxane composition of the present invention can be prepared in particulate form with a median diameter based on volume falling within a range of 5 to 50 μm. The median diameter based on volume of the solid polymethylaluminoxane composition of the present invention in particulate form kept within this range maintains a good polymer bulk density using the solid polymethylaluminoxane composition and a transition metal compound, and yields an olefin polymer in which the production of micropowder polymer is inhibited. From the perspective of achieving good powder properties expressed by bulk density and the like in the olefin polymer obtained, a median diameter based on volume of the solid polymethylaluminoxane composition of about 5 to 200 μm is generally considered good.

However, when homogeneity is taken into account, the median diameter based on volume of the solid polymethylaluminoxane composition of the present invention is desirably 5 to 50 μm, preferably falling within a range of 5 to 40 μm, and more preferably, falling within a range of 5 to 30 μm.

The median diameter based on volume and the particle size distribution of the solid polymethylaluminoxane composition of the present invention can be determined by the laser diffraction and scattering method under a dry nitrogen atmosphere using a Master Sizer 2000 Hydro S made by Malvern Instrument Ltd. The specific method is described in the embodiments.

The solid polymethylaluminoxane composition of the present invention is particulate and the specific surface area desirably falls within a range of 10 to 25 m²/mmol-Al. The specific surface area of the particulate solid polymethylaluminoxane composition of the present invention kept within this range exhibits good activity in polymerization of the olefin compound using the solid polymethylaluminoxane composition and a transition metal compound. Here, the phrase "good activity" desirably means equivalent to the activity achieved when employing the polymethylaluminoxane composition in solution form. However, good polymerization activity of the solid polymethylaluminoxane composition of the present invention does not depend on the specific surface area alone, and could conceivably depend on components and structures in addition to the specific surface area of the solid polymethylaluminoxane composition. The specific surface area could conceivably affect activation caused by contact of the catalyst of the transition metal compound, including the metallocene compound serving as the primary catalyst, with the solid polymethylaluminoxane composition in the course of employing them to polymerize an olefin. That is, a low specific surface area is generally thought to result in poor primary catalyst activation efficiency, and a high specific surface area in high activation efficiency. However, an excessively high specific surface area is thought to result in excessive porous structure formed in the interior of the solid polymethylaluminoxane composition and in a drop in the strength of the solid. For these reasons, the specific surface area desirably falls within a range of 10 to 25 m²/mmol-Al, preferably within a range of 13 to 22 m²/mmol-Al.

The specific surface area of the solid polymethylaluminoxane composition of the present invention can be determined using the gas adsorption phenomenon in a solid surface by a BET adsorption isotherm. The specific method is described in the embodiments.

The solubility in n-hexane at 25° C. of the solid polymethylaluminoxane composition of the present invention is desirably 0 to 2 mol %, and its solubility in toluene at 25° C. is desirably 0 to 2 mol %.

The solid polymethylaluminoxane composition of the present invention is characterized by extremely low solubility in toluene and in n-hexane maintained at a temperature of 25° C. It satisfies 0 to 2 mol %, desirably 0 to 1 mol %, and preferably, a range of 0 to 0.2 mol % for n-hexane. It satisfies 0 to 2 mol %, desirably 0 to 1 mol %, and preferably, a range of 0 to 0.5 mol % for toluene. The solubility in solvents can be measured by the method described in JP-B (KOKOKU)-H07-42301. Specific details are given in the embodiments.

The solid polymethylaluminoxane composition of the present invention does not contain $SiO_2$. In the solid polymethylaluminoxane composition of the present invention, $SiO_2$ is not positively incorporated in at least the manufacturing process. By not containing $SiO_2$, the solid polymethylaluminoxane composition of the present invention avoids the drawbacks of solid polymethylaluminoxane compositions containing $SiO_2$.

[The Method for Manufacturing a Solid Polymethylaluminoxane Composition]

The method for manufacturing the solid polymethylaluminoxane composition of the present invention comprises the step of:

(a) heating an aromatic hydrocarbon solution containing polymethylaluminoxane containing the unit denoted by general formula (II) below and trimethylaluminum (polymethylaluminoxane composition in solution) to precipitate a solid polymethylaluminoxane composition containing polymethylaluminoxane and trimethylaluminum:

-[(Me)AlO]$_n$—            (II)

(wherein n denotes an integer of from 1 to 50).

The phrase "containing the unit denoted by general formula (II)" means containing polymethylaluminoxane in which n denotes a single number falling within the above range (n being a specified integer) or containing multiple polymethylaluminoxanes of multiple types within the above range (n denoting multiple different integers). The reason n denotes an integer of from 10 to 50 is to make the degree of polymerization of the aluminoxane based on molecular weight as calculated from the drop in the solidification point in benzene fall within a range of 10 to 50.

The polymethylaluminoxane composition that is employed as a starting material in the manufacturing method of the present invention can be prepared, for example, by the method described in Patent Reference 17. The method described in Patent Reference 17 prepares a polymethylaluminoxane composition without hydrolyzing trimethylaluminum. Specifically, an alkylaluminum compound having an aluminum-oxygen-carbon bond is thermally decomposed to obtain a polymethylaluminoxane composition in solution form.

The aromatic hydrocarbon that is employed in the polymethylaluminoxane composition in solution is, for example, benzene, toluene, ethylbenzene, propylbenzene, butylbenzene, xylene, chlorobenzene, dichlorobenzene or the like. However, it is not limited to these examples. Any aromatic hydrocarbon can be employed in the polymethylaluminoxane compound in solution.

The alkylaluminum compound having an aluminum-oxygen-carbon bond is desirably prepared by reacting trimethylaluminum and an oxygen-containing organic compound. Further, the oxygen-containing organic compound is desirably an aliphatic or aromatic carboxylic acid denoted by general formula (III).

R¹—(COOH)$_n$            (III)

(wherein R¹ denotes a hydrocarbon group in the form of a C1 to C20 linear or branched alkyl group, alkenyl group, or aryl group, and n denotes an integer of 1 to 5).

Examples of the oxygen-containing compound employed in the reaction of the oxygen-containing compound and a trimethylaluminum in the form of an alkylaluminum compound having an aluminum-oxygen-carbon bond giving the polymethylaluminoxane composition in solution through a thermal decomposition reaction are: carboxylic acid compounds having COOH groups and carboxylic anhydrides. In the preparation of the polymethylaluminoxane composition in solution, a single compound or multiple compounds can be employed. Specific examples of the oxygen-containing compound are: formic acid, acetic acid, propionic acid, n-butyric acid, n-valeric acid, n-caproic acid, n-enanthic acid, n-caprylic acid, n-pelargonic acid, n-capric acid, n-lauric acid, n-myristic acid, n-stearic acid, oxalic acid, malonic acid, succinic acid, glutaric acid, adipic acid, pimelic acid, suberic acid, azelaic acid, sebacic acid, benzoic acid, phthalic acid, citric acid, tartaric acid, lactic acid, malic acid, toluic acid, toluic anhydride, acetic anhydride, propionic anhydride, n-butyric anhydride, n-valeric anhydride, n-caproic anhydride, oxalic anhydride, malonic anhydride, succinic anhydride, glutaric anhydride, benzoic anhydride, phthalic anhydride, and toluic anhydride. Of these, desirable examples are acetic acid, acetic anhydride, propionic acid, propionic anhydride, benzoic acid, benzoic anhydride, phthalic acid, phthalic anhydride, toluic acid, and toluic anhydride.

The mole ratio of the aluminum atoms contained in the trimethylaluminum and the oxygen atoms of the oxygen-containing organic compound employed in synthesis of the polymethylaluminoxane composition in solution can be set as desired to control the molecular weight of the polymethylaluminoxane or the residual quantity of trimethylaluminum. The ratio of the molar mass of the aluminum atoms contained in the trimethylaluminum to the oxygen atoms of the oxygen-containing organic compound can be set optionally within a range of 0.5 to 3.0:1.

From the perspectives of the ease of preparation of the polymethylaluminoxane composition in solution, the stability thereof, and suitably controlling the quantity of residual trimethylaluminum, the above molar mass ratio desirably falls within a range of 1.0 to 1.7:1, preferably within a range of 1.15 to 1.4:1, and more preferably, within a range of 1.2 to 1.4:1.

The thermal decomposition temperature of the aluminum compound having an aluminum-oxygen-carbon bond that is the precursor of the polymethylaluminoxane composition in solution can be set to any temperature between 20 to 90° C. From the perspectives of ease of operation and safety of reaction, and a suitable reaction time, the thermal decomposition temperature is desirably 30 to 80° C., preferably 60 to 80° C. The thermal decomposition time of the aluminum compound having an aluminum-oxygen-carbon bond varies with the thermal decomposition temperature and the composition of the starting materials (for example, the Al/O mole ratio), but can fall within a range of 5 to 100 hours, for example. A low temperature requires a long time, while a high temperature makes it possible to rapidly complete thermal decomposition.

A thermal decomposition temperature exceeding 100° C. causes the marked production of gel products, and results in a drop in the recovery yield of the uniform solution of polymethylaluminoxane. Conversely, a thermal decomposition temperature below 50° C. sometimes causes a pronounced drop in productivity due to an increase in the polymethylaluminoxane production reaction time.

Control of the temperature is important during preparation of the polymethylaluminoxane composition in solution that is employed as a starting material in the present invention. At first glance, the present invention would seem to be part of the process of preparing the polymethylaluminoxane composition in solution. When attempting to obtain a solid polymethylaluminoxane composition of controlled particle diameter, it is impossible to obtain the solid polymethylaluminoxane composition directly, without obtaining a polymethylaluminoxane composition in solution by thermally decomposing the alkylaluminum compound having an aluminum-oxygen-carbon bond that is a starting material of the polymethylaluminoxane compound in solution. First, a polymethylaluminoxane composition in solution is prepared by thermally decomposing the alkylaluminum compound having an aluminum-oxygen-carbon bond. Only when the polymethylaluminoxane composition in solution that has been prepared is heated under prescribed conditions the solid polymethylaluminoxane composition is obtained. For example, even when the starting material polymethylaluminoxane composition is directly heated to 100° C., no solid polymethylaluminoxane composition of uniform particle diameter is obtained. The reason is currently unclear. However, the present inventors believe that if the solid polymethylaluminoxane composition of stable particle diameter in terms of energy is thought of as being formed by self-association of polymethylaluminoxane of a given chain length and chain length distribution, a properly formed polymethylaluminoxane structure can be understood as being necessary.

A concentration of the polymethylaluminoxane in the inactive hydrocarbon solvent falling within range of 6 to 40 wt % is adequate, 6 to 30 wt % is desirable, and 10 to 25 wt % is preferable.

In the great majority of the literature describing the obtaining of a polymethylaluminoxane composition in solution by the thermal decomposition reaction of an aluminum compound having an aluminum-oxygen-carbon bond, the focus is on obtaining a polymethylaluminoxane composition in solution at a quantitative reaction yield and on being able to control the quantity of trimethylaluminum in the polymethylaluminoxane composition in solution. Generally, the trimethylaluminum does not function as an activation agent of transition metal compounds, including metallocene compounds. Thus, controlling the quantity of trimethylaluminum remaining in the polymethylaluminoxane composition in solution is an important issue. Additionally, when preparing a polymethylaluminoxane composition in solution by hydrolysis, it is known that the aluminum recovery rate will drop steeply unless the aluminum concentration in the reaction solution is reduced and the quantity of water introduced is kept low relative to the starting material trimethylaluminum.

In the polymethylaluminoxane composition in solution that is employed as a starting material, it is desirable for the mole fraction of the methyl groups derived from the trimethylaluminum component relative to the total number of moles of methyl groups to be 15 mol % or less from the perspective of increasing the yield of solid polymethylaluminoxane. The mole fraction of methyl groups derived from the trimethylaluminum component relative to the total number of moles of methyl groups is desirably 14 mol % or lower. The lower limit of the mole fraction of methyl groups derived from the trimethylaluminum component relative to the total number of moles of methyl groups is about 6 mol %. The polymethylaluminoxane composition in solution that is prepared by hydrolysis has a mole fraction of methyl groups derived from the trimethylaluminum component relative to the total number of moles of methyl groups of 40 to 50 mol %. It is difficult to lower the mole fraction of methyl groups derived from the trimethylaluminum component relative to the total number of moles of methyl groups in the methylaluminoxane composition below 15 mol % by the usual concentration and drying processes. By making the mole ratio of oxygen atoms in the oxygen-containing organic compound and aluminum atoms contained in the trimethylaluminum 1.15 when preparing the polymethylaluminoxane composition in solution by thermal decomposition, it becomes possible to achieve a lower limit of the mole fraction of methyl groups derived from the trimethylaluminum component relative to the total number of moles of methyl groups of 8 mol %, and the performance of the solid polymethylaluminoxane composition obtained is good. By employing a mole ratio of oxygen atoms in the oxygen-containing organic compound and aluminum atoms in the trimethylaluminum of 1.10, a mole fraction of methyl groups derived from the trimethylaluminum component relative to the total number of moles of methyl groups of 5.2 mol % can be achieved, but the performance of the solid polymethylaluminoxane composition obtained is poor. For these reasons, 8 to 14 mol % is desirable.

The aromatic hydrocarbon employed in the manufacturing method of the present invention is not specifically limited. Examples are: benzene, toluene, ethylbenzene, propylbenzene, butylbenzene, xylene, chlorobenzene, cyclobenzene and the like.

In step (a), a heating temperature and a heating time suited to precipitation of the solid polymethylaluminoxane composition are desirably selected from:

(i) a heating temperature falling within a range of 80 to 200° C., and (ii) a heating time of from 5 minutes or more to less than 24 hours.

When heating of the aromatic hydrocarbon solution of trimethylaluminum and polymethylaluminoxane containing the unit denoted by general formula (II) (the polymethylaluminoxane composition in solution) is continued at the prescribed temperature, a solid polymethylaluminoxane composition containing trimethylaluminum and polymethylaluminoxane was discovered by the present inventors to precipitate in the solution in a form with uniform particle diameters. The prescribed temperature falls within a range of 80 to 200° C. The time required for precipitation varies with the temperature, but falls, for example, within a range of from 5 minutes or more to less than 24 hours. By remaining within this range, it is possible to obtain at high yield particles of the solid polymethylaluminoxane composition of desired particle diameter and uniform particle diameter. However, depending on the heating temperature, there are cases where a heating time exceeding this range is suitable. Precipitation of the solid polymethylaluminoxane composition in the solution increases with time, and once it has reached a certain level, there is no further increase in the quantity of the precipitate. The quantity (recovery rate) of precipitate varies with the composition (variation of components and their amount) of the polymethylaluminoxane composition and the concentration of the solute in the solvent (aromatic hydrocarbon solution).

Taking into account the particle diameter, particle diameter homogeneity, yield, and the like of the solid polymethylaluminoxane composition particles, a heating temperature of 80 to 200° C. will suffice, 90 to 150° C. is desirable, and 100 to 130° C. is preferable. Within this temperature range, the time is desirably 1 to 20 hours, preferably 5 to 12 hours. However, when the temperature is low, the time required for solid polymethylaluminoxane composition particles to precipitate increases. When the temperature is high, the time required for solid polymethylaluminoxane composition particle to precipitate tends to decrease.

The manufacturing method of the present invention can further comprise a step (b) of washing the solid polymethylaluminoxane composition that has been precipitated by heating with a nonaromatic hydrocarbon solvent. Examples of the nonaromatic hydrocarbon solvent that is employed for washing are: n-pentane, n-hexane, cyclohexane, methylcyclohexane, ethylcyclohexane, n-heptane, n-octane, n-decane, n-undecane, Isopar E and the like. In the present invention, the nonaromatic solvent is employed, not to precipitate the solid polymethylaluminoxane composition as is seen in prior art, but to facilitate washing and drying of the solid polymethylaluminoxane composition that has been precipitated by heating. Thus, a solvent with a low boiling point that facilitates the operation of drying the solid polymethylaluminoxane, specifically, n-pentane, n-hexane, or cyclohexane, is desirable.

In step (b), the nonaromatic hydrocarbon solvent can be added in a quantity of four equivalents by volume or greater to the polymethylaluminoxane composition that has been heated in step (a). The use of such a quantity affords the advantages of reducing the amount of residual aromatic solvent and facilitating drying of the solid polymethylaluminoxane composition obtained.

In the above manufacturing method, the solid polymethylaluminoxane composition of the present invention can be dispersed in solvent, or the solvent can be removed and the composition dried to obtain a powder. The powder can be dried, for example, by the method of removing the solvent under reduced pressure or the method of employing a dry, hot nitrogen flow. In contrast to the case of a polymethylaluminoxane composition in solution, the sole goal of drying the solid polymethylaluminoxane composition of the present invention is to eliminate solvent adsorbing to the solid. Thus, since there is no scattering or the like of trimethylaluminum, a vacuum pump can be employed without problem.

[The Olefin Polymerization Catalyst]

The present invention includes an olefin polymerization catalyst. The olefin polymerization catalyst of the present invention contains catalytic components in the form of the solid polymethylaluminoxane composition of the present invention and the transition metal compound denoted by general formula (IV) below:

$$MR^5R^6R^7R^8 \quad (IV)$$

(wherein M denotes a transition metal element, and $R^5$, $R^6$, $R^7$, and $R^8$, which are joined together, denote organic groups having a cycloalkadienyl skeleton, alkyl groups, alkoxy groups, aryloxy groups, alkylsilyl groups, alkylamide groups, alkylimide groups, alkylamino groups, alkylimino groups, or halogen atoms).

The solid polymethylaluminoxane composition of the present invention can be combined with a known olefin polymerization catalyst and employed as a polymerization catalyst. Transition metal compounds are examples of olefin polymerization catalysts. The transition metal compound can be one denoted by general formula (IV).

Specific examples of M in general formula (IV) are titanium, zirconium, hafnium, chromium, vanadium, manganese, iron, cobalt, nickel, and palladium; desirable examples are titanium, zirconium, chromium, iron, and nickel.

In general formula (IV), a metallocene compound coordinated with one or two ligands having cycloalkadienyl skeletons is desirable as the transition metal compound. Examples of ligands having cycloalkadienyl skeletons are cyclopentadienyl groups, methylcyclopentadienyl groups, ethylcyclopentadienyl groups, butylcyclopentadienyl groups, dimethylcyclopentadienyl groups, pentamethylcyclopentadienyl groups, and other alkyl-substituted cyclopentadienyl groups; indenyl groups; and fluorenyl groups. The cycloalkadienyl groups can be crosslinked with divalent substituted alkylene groups, substituted silylene groups, or the like.

Ligands other than ligands having cycloalkadienyl skeletons are: hydrocarbon groups with 1 to 20 carbon atoms, alkoxy groups, aryloxy groups, alkylsilyl groups, amino groups, imino groups, halogen atoms, and hydrogen atoms. Examples of hydrocarbon groups with 1 to 20 carbon atoms are alkyl groups, cycloalkyl groups, aryl groups, and aralkyl groups. Specific examples of alkyl groups are methyl groups, ethyl groups, propyl groups, isopropyl groups, and butyl groups. Specific examples of cycloalkyl groups are cyclopentyl groups and cyclohexyl groups. Specific examples of aryl groups are phenyl groups and tolyl groups. A specific example of an aralkyl group is a benzyl group. Specific examples of alkoxy groups are methoxy groups, ethoxy groups, and butoxy groups. A specific example of an aryloxy group is a phenoxy group. These groups may have substituents in the form of halogen atoms or the like. Examples of alkylsilyl groups are trimethylsilyl groups and triethylsilyl groups. Examples of halogen are fluorine, chlorine, bromine, and iodine.

Specific examples of transition metal compounds containing ligands having cycloalkadienyl skeletons when M denotes zirconium in general formula (IV) above are: bis(cyclopentadienyl)zirconium monochloride monohydride, bis(cyclopentadienyl)zirconium monobromide monohydride, bis(cyclopentadienyl)methylzirconium hydride, bis(cyclopentadienyl)ethylzirconium hydride, bis(cyclopentadienyl)phenylzirconium hydride, bis(cyclopentadienyl)benzylzirconium hydride, bis(cyclopentadienyl)neopentylzirconium hydride, bis(methylcyclopentadienyl)zirconium monochloride hydride, bis(indenyl)zirconiummonochloride hydride, bis(cyclopentadienyl)zirconium dichloride, bis(cyclopentadienyl)zirconium dibromide, bis(cyclopentadienyl)methylzirconium monochloride, bis(cyclopentadienyl)ethylzirconium monochloride, bis(cyclopentadienyl)cyclohexylzirconium monochloride, bis(cyclopentadienyl)phenylzirconium monochloride, bis(cyclopentadienyl)benzylzirconium monochloride, bis(methylcyclopentadienyl)zirconium dichloride, bis(dimethylcyclopentadienyl)zirconium dichloride, bis(n-butylcyclopentadienyl)zirconium dichloride, bis(indenyl)zirconium dichloride, bis(indenyl)zirconium dibromide, bis(cyclopentadienyl)zirconium dimethyl, bis(cyclopentadienyl)zirconium diphenyl, bis(cyclopentadienyl)zirconium dibenzyl, bis(cyclopentadienyl)zirconium monomethoxymonochloride, bis(cyclopentadienyl)zirconium monoethoxymonochloride, bis(methylcyclopentadienyl)zirconium monoethoxmonochloride, bis(cyclopentadienyl)zirconium monophenoxmonochloride, and bis(fluorenyl)zirconium dichloride and the like.

Specific examples of transition metal compounds containing at least two ligands having cycloalkadienyl skeletons, with the at least two ligands having cycloalkadienyl skeletons being bonded via alkylene groups such as ethylene groups or propylene groups; substituted alkylene groups such as isopropylidene and diphenylmethylene; silylene groups; substituted silylene groups such as dimethylsilylene groups; or the like when M denotes zirconium in general formula (IV) are: ethylene bis(indenyl)dimethylzirconium, ethylene bis(indenyl)diethylzirconium, ethylene bis(indenyl)diphenylzirconium, ethylene bis(indenyl)methylzirconium monochloride, ethylene bis(indenyl)ethylzirconium monochloride, ethylene bis(indenyl)methylzirconium monobromide, ethylene bis(indenyl)zirconium dichloride, ethylene bis(indenyl)zirconium dibromide, ethylene bis(4,5,6-tetrahydro-1-indenyl)zirconium dichloride and the like. These may be racemic compounds, meso compounds, or a mixture thereof.

A single one of these transition metal compounds may be employed in homogeneous polymerization, or two or more may be employed to adjust the molecular weight distribution or the like. When preparing a solid catalyst in advance, a single one of these transition metal compounds may be employed, or two or more may be employed to adjust the molecular weight distribution or the like.

[The Method for Manufacturing Polyolefins]

The present invention includes a method for manufacturing polyolefins comprising polymerizing an olefin using the above-described catalyst of the present invention.

Homogeneous polymerization using the solid polymethylaluminoxane composition of the present invention and polymerization employing a supported catalyst prepared using the solid polymethylaluminoxane composition of the present invention exhibit suitable properties in any form of polymerization, such as solution polymerization employing a solvent, bulk polymerization not employing a solvent, and vapor phase polymerization. Desirable properties are exhibited in any method such as continuous polymerization and batch polymerization, and hydrogen or the like can be used as needed as a molecular weight-adjusting agent.

The monomer employed in polymerization can be any compound such as a single olefin monomer or a combination of the single olefin monomers which are co-polymerizable. Specific examples are: ethylene, propylene, 1-butene, 1-pentene, 1-hexene, 1-decene, 1-hexadecene, 1-octadecene, 1-eicocene, and other a (alpha)-olefins; bisfluoroethylene, trifluoroethylene, tetrafluoroethylene, hexafluoropropene, and other halogen-substituted olefins; and cyclopentene, cyclohexene, norbornene, and other cyclic olefins.

EMBODIMENTS

The present invention is described in detail below through embodiments. However, the present invention is not limited to the embodiments.

In the embodiments set forth below, the solid polymethylaluminoxane composition was normally dried under a full vacuum with a vacuum pump at 40° C. through a sealed pot containing liquid paraffin. The drying was ended when no bubbles were observed in the sealed pot.

[Test Methods]

(1) Solubility

The solubility of the solid polymethylaluminoxane composition of the present invention in n-hexane and in toluene maintained at a temperature of 25° C. was measured according to the method described in JP-B (KOKOKU)-H07-42301. Specifically, the solubility in n-hexane was determined by adding 2 g of the solid polymethylaluminoxane composition to 50 mL of n-hexane maintained at 25° C., stirring for two hours, separating the solution with a G-4 glass filter, and measuring the aluminum concentration in the filtrate. The solubility measured by this method was determined to be the ratio of the aluminum atoms present in the filtrate to the quantity of aluminum atoms equivalent to 2 g of the solid polymethylaluminoxane composition employed as the sample.

(2) The Aluminum Content

The aluminum content of the polymethylaluminoxane composition in solution and the solid polymethylaluminoxane composition was determined by adding an excessive quantity of disodium ethylenediaminetetraacetate to a solution that had been hydrolyzed with 0.5 N sulfuric acid aqueous solution and then conducting reverse titration with zinc sulfate using dithizone as indicator. When the measured concentration was dilute, measurement was conducted by atomic absorption analysis.

(3) The Specific Surface Area of the Solid Aluminoxane Composition

The specific surface area of the solid aluminoxane composition was determined using the gas adsorption phenomenon in the solid surface by a BET adsorption isotherm. A BEL- SORP mini II made by BEL JAPAN, INC. was employed as the measurement device and nitrogen gas was employed as the measurement gas.

(4) The Particle Size Distribution and Median Diameter Based on Volume of the Solid Aluminoxane Composition The particle size distribution and median diameter based on volume of the solid aluminoxane composition were determined by the laser diffraction and scattering method under a dry nitrogen atmosphere with a Master Sizer 2000 Hydro S made by Malvern Instrument Ltd. Dehydrated and degassed n-hexane was employed as the primary dispersion medium, with dehydrated and degassed toluene being employed as one portion for some purposes. Homogeneity was defined by the equation given below as an index of the catalyst particle size distribution:

Homogeneity=Σ(SIGMA)$Xi$|$d(0.5)$−$Di$|/$d(0.5)$Σ(SIGMA)$Xi$ (wherein $Xi$ denotes the histogram value of a particle i, $d(0.5)$ denotes the median diameter based on volume, and $Di$ denotes the diameter based on volume of particle i).

(5) The Mole Fraction of Methyl Groups

The mole fractions of the various components in the polymethylaluminoxane composition were determined from the surface area ratios assigned to the various components in $^1$H-NMR measurement of the polymethylaluminoxane composition. The example of obtaining the mole fractions of the specific Me(PMAO) and Me(TMAL) of the polymethylaluminoxane composition will be given below. Me(PMAO) denotes the mole fraction of methyl groups derived from polymethylaluminoxane. Me(TMAL) denotes the mole fraction of methyl groups derived from trimethylaluminum.

First, $^1$H-NMR measurement of the polymethylaluminoxane is conducted with $d_8$-THF as the deuterated solvent. The $^1$H-NMR measurement is conducted at a measurement temperature of 24° C. with a 300 MHz Gemini 2000 NMR measurement device made by Varian Technologies Japan, Ltd. FIG. 1 shows an example of a $^1$H-NMR chart.

(i) The integral value of all Me group peaks of the polymethylaluminoxane containing trimethylaluminoxane appearing at from about −0.3 ppm to −1.2 ppm is determined and denoted as I (polymethylaluminoxane).

(ii) The Me group peak derived from TMAL in the vicinity of −1.1 ppm is cut with the −1 tangent and the integral value I (TMAL-Me) is obtained.

(iii) The various integral values obtained in (ii) are subtracted from the integral values I (polymethylaluminoxane) obtained in (i) to obtain the integral value I (PMAO-Me) of just the Me groups of the polymethylaluminoxane not containing trimethylaluminum. When I (TMAL-Me) and I (PMAO-Me) are normalized by being divided by I (polymethylaluminoxane), the mole fractions of Me (PMAO) and Me (TMAL) are obtained.

The various peaks can be readily cut out by methods employing commercial curve fitting programs, methods employing baseline collection, and the like.

Further, the analysis sample of the polymethylaluminoxane composition in solvent was prepared by adding about 0.5 mL of $d_8$-THF to about 0.05 mL of polymethylaluminoxane composition in solution. The analysis sample of the solid polymethylaluminoxane composition was prepared by adding about 0.5 mL of $d_8$-THF to about 10 mg of polymethylaluminoxane composition in solution.

The following reactions were conducted in a dry nitrogen gas atmosphere. Dehydrated and degassed solvent was employed.

Preliminary Test 1 (Benzoic Acid-Al/O=1.40)

(1) Synthesis of Polymethylaluminoxane Composition in Solution

To a separable flask with an interior volume of 2 L equipped with stirrer were added 240.8 g (3.34 mol) of trimethylaluminum (TMAL) and 600.5 g of toluene. The solution was cooled to 15° C. To the solution was gradually added 145.7 g (1.19 mol) of benzoic acid at a rate that caused the temperature of the solution to drop to 25° C. or below. The mixture was then heated and aged at 50° C. for one hour. At that time, the mole ratio of the oxygen atoms of benzoic acid and the TMAL was 1.40. The reaction solution was heated for four hours at 70° C. and then heated for six hours at 60° C. to obtain a toluene solution of polymethylaluminoxane. The solution obtained was a transparent liquid free of gelled material. The results of aluminum analysis conducted following recovery of the reaction solution indicated the quantitative reaction yield based on aluminum atoms. The aluminum concentration of the reaction solution obtained was 9.30 mass %. The quantity of Me(TMAL) in the polymethylaluminoxane composition in solution obtained was determined by $^1$H-NMR to be 26.0 mol %. Since the polymethylaluminoxane composition was in solution form, the solubility measurement given in the test methodology section was precluded. However, the concentration in toluene, determined by calculation from the specific gravity of the solution and the aluminum concentration, was about 3.1 mol/L.

The molecular weight determined by dissolving polymethylaluminoxane that had been concentrated and dried in benzene and employing the drop in solidification point method was 2,430. Accordingly, the degree of polymerization n of the aluminoxane was determined to be 42.

(2) Evaluation of Ethylene Polymerization

1. Polymerization Using Bis(Cyclopentadienyl)Zirconium Dichloride

To a 500 mL four-necked flask equipped with magnetic stirrer was charged 250 mL of toluene. The toluene was heated to 34° C. To this was added a toluene solution of 0.16 g (5.93 mmol) of polymethylaluminoxane based on aluminum atoms. Bis(cyclopentadienyl)zirconium dichloride ($Cp_2ZrCl_2$) was added to achieve an Al/Zr mole ratio of 5,000. While raising the temperature to 40° C., ethylene gas was blown in. After 10 minutes, the ethylene gas feed was halted and methanol was introduced to deactivate the catalyst. The polyethylene produced was filtered and dried. The polymerization activity was calculated to be $62 \times 10^6$ g-PE/mol-Zr·atm·hr. The polymer was amorphous and there was pronounced fouling of the polymerization apparatus.

2. Polymerization Employing Bis(N-Butylcyclopentadienyl) Zirconium Dichloride

To a 500 mL four-necked flask equipped with magnetic stirrer was charged 250 mL of toluene. The toluene was heated to 34° C. To this was added a toluene solution of 0.043 g (1.6 mmol) of polymethylaluminoxane composition based on aluminum atoms. Bis(n-butylcyclopentadienyl)zirconium dichloride ($(nBu-Cp)_2ZrCl_2$) was added to achieve an Al/Zr mole ratio of 5,000. While raising the temperature to 40° C., ethylene gas was blown in. After 10 minutes, the ethylene gas feed was halted and methanol was introduced to deactivate the catalyst. The polyethylene produced was filtered and dried. The polymerization activity was calculated to be $35 \times 10^6$ g-PE/mol-Zr·atm·hr.

3. Polymerization Employing Rac-Ethylenebis(4,5,6-Tetrahydro-1-Indenyl)Zirconium Dichloride To a 500 mL four-necked flask equipped with magnetic stirrer was charged 250 mL of toluene. The toluene was heated to 34° C. To this was added a toluene solution of 0.035 g (1.3 mmol) of polymethylaluminoxane based on aluminum atoms. Rac-ethylene bis(4,5,6-tetrahydro-1-indenyl)zirconium dichloride (rac-Et(Ind)$_2$ZrCl$_2$) was added to achieve an Al/Zr mole ratio of 5,000. While raising the temperature to 40° C., ethylene gas was blown in. After 10 minutes, the ethylene gas feed was halted and methanol was introduced to deactivate the catalyst. The polyethylene that had been produced was filtered and dried. The polymerization activity was calculated to be 25×10$^6$ g-PE/mol-Zr·atm·hr.

Preliminary Test 2 (Benzoic Acid-Al/O=1.30)
(1) Synthesis of Polymethylaluminoxane Composition in Solution With the exceptions that the quantity of benzoic acid introduced into the powder was changed so that the mole ratio of oxygen atoms in the benzoic acid and the TMAL was 1.30 and the heating following aging by heating to 50° C. was changed to heating at 70° C. for 15 hours in Preliminary Test 1, a polymethylaluminoxane composition in solution was synthesized in the same manner as in Preliminary Test 1. The solution obtained was a transparent liquid free of gelled material. The results of aluminum analysis conducted following recovery of the reaction solution indicated the quantitative reaction yield based on aluminum atoms. The aluminum concentration of the reaction solution obtained was 9.40 mass %. The quantity of Me(TMAL) in the polymethylaluminoxane composition in solution obtained was determined by $^1$H-NMR to be 18.3 mol %. Since the polymethylaluminoxane composition was in solution form, the solubility measurement described in the test methodology section was precluded. However, the concentration in toluene, determined by calculation from the specific gravity of the solution and the aluminum concentration, was about 3.1 mol/L.

(2) Ethylene Polymerization Evaluation

Polymerization evaluation by the same method as that described in (2)1. of Preliminary Test 1 revealed the polymerization activity to be 45×10$^6$ g-PE/mol-Zr·atm·hr. The polymer was amorphous and there was pronounced fouling of the polymerization apparatus.

Preliminary Test 3 (Benzoic Acid-Al/O=1.25)
(1) Synthesis of Polymethylaluminoxane Composition in Solution With the exceptions that the quantity of benzoic acid introduced into the powder was changed so that the mole ratio of oxygen atoms in the TMAL and the benzoic acid was 1.25 and the heating following aging by heating to 50° C. was changed to heating at 70° C. for 21 hours in Preliminary Test 1, a polymethylaluminoxane composition in solution was synthesized in the same manner as in Preliminary Test 1. The solution obtained was a transparent liquid free of gelled material. The results of aluminum analysis conducted following recovery of the reaction solution indicated the quantitative reaction yield based on aluminum atoms. The aluminum concentration of the reaction solution obtained was 9.15 mass %. The quantity of Me(TMAL) in the polymethylaluminoxane composition in solution obtained was determined by $^1$H-NMR to be 17.5 mol %. Since the polymethylaluminoxane composition was in solution form, the solubility measurement given in the test methodology section was precluded. However, the concentration in toluene, determined by calculation from the specific gravity of the solution and the aluminum concentration, was about 3.1 mol/L.

(2) Ethylene Polymerization Evaluation

Polymerization evaluation by the same method as that described in (2)1. of Preliminary Test 1 revealed the polymerization activity to be 49×10$^6$ g-PE/mol-Zr·atm·hr. The polymer was amorphous and there was pronounced fouling of the polymerization apparatus.

Preliminary Test 4 (Benzoic Acid-Al/O=1.20)

With the exceptions that the quantity of benzoic acid introduced into the powder was changed so that the mole ratio of oxygen atoms in the TMAL and the benzoic acid was 1.20 and the heating following aging by heating to 50° C. was changed to heating at 70° C. for 32 hours in Preliminary Test 1, a polymethylaluminoxane composition in solution was synthesized in the same manner as in Preliminary Test 1. The solution obtained was a transparent liquid free of gelled material. The results of aluminum analysis conducted following recovery of the reaction solution indicated the quantitative reaction yield based on aluminum atoms. The aluminum concentration of the reaction solution obtained was 9.04 mass %. The quantity of Me(TMAL) in the polymethylaluminoxane composition in solution obtained was determined by $^1$H-NMR to be 14.0 mol %. Since the polymethylaluminoxane composition was in solution form, the solubility measurement given in the test methodology section was precluded. However, the concentration in toluene, determined by calculation from the specific gravity of the solution and the aluminum concentration, was about 3.0 mol/L.

(2) Ethylene Polymerization Evaluation

Polymerization evaluation by the same method as that described in (2)1. of Preliminary Test 1 revealed the polymerization activity to be 39×10$^6$ g-PE/mol-Zr·atm·hr. The polymer was amorphous. High-temperature GPC revealed the molecular weight to be 180,000 and the Mw/Mn to be 2.9. The polymer was amorphous and there was pronounced fouling of the polymerization apparatus.

2. Polymerization Employing Bis(N-Butylcyclopentadienyl) Zirconium Dichloride

Polymerization evaluation by the same method as that described in (2)2. of Preliminary Test 1 revealed the polymerization activity to be 70×10$^6$ g-PE/mol-Zr·atm·hr. The polymer was amorphous and there was pronounced fouling of the polymerization apparatus.

3. Polymerization Employing Rac-Ethylenebis(4,5,6-Tetrahydro-1-Indenyl)Dizirconium Dichloride Polymerization evaluation by the same method as that described in (2)3. of Preliminary Test 1 revealed the polymerization activity to be 35×10$^6$ g-PE/mol-Zr·atm·hr. The polymer was amorphous and there was pronounced fouling of the polymerization apparatus.

Preliminary Test 5 (Benzoic Acid-Al/O=1.10)
(1) Synthesis of Polymethylaluminoxane Composition in Solution With the exceptions that the quantity of benzoic acid introduced into the powder was changed so that the mole ratio of oxygen atoms in the TMAL and the benzoic acid was 1.10 and the heating following aging by heating to 50° C. was changed to heating at 70° C. for 60 hours in Preliminary Test 1, a polymethylaluminoxane composition in solution was synthesized in the same manner as in Preliminary Test 1. The solution obtained was a transparent viscous liquid free of gelled material. The results of aluminum analysis conducted following recovery of the reaction solution indicated the quantitative reaction yield based on aluminum atoms. The aluminum concentration of the reaction solution obtained was 8.81 mass %. The quantity of Me(TMAL) in the polymethylaluminoxane composition in solution obtained was determined by $^1$H-NMR to be 5.2 mol %. Since the polymethylaluminoxane composition was in solution form, the solubility measurement given in the test methodology section was precluded. However, the concentration in toluene, determined by calculation from the specific gravity of the solution and the aluminum concentration, was about 2.9 mol/L.

(2) Ethylene Polymerization Evaluation

Polymerization evaluation by the same method as that described in (2)1. of Preliminary Test 1 revealed the polymerization activity to be $46 \times 10^6$ g-PE/mol-Zr·atm·hr. The polymer was amorphous and there was pronounced fouling of the polymerization apparatus.

Preliminary Test 6 (Acetophenone-Al/O=1.39)

(1) Synthesis of Polymethylaluminoxane Composition in Solution

To a separable flask with an internal volume of 500 mL equipped with stirrer were added 68.39 g (948.81 mmol) of trimethylaluminum (TMAL) and 102.51 g of toluene. The solution was cooled to 15° C. To the solution was gradually added a solution of 82.13 g (683.56 mol) of acetophenone and 19.35 g of toluene at a rate that caused the temperature within the flask to remain at 25° C. or below. The mixture was then heated and aged at 50° C. for one hour. At that time, the mole ratio of the oxygen atoms of acetophenone and the TMAL was 1.39. To the reaction solution was added in a single installment a thermal decomposition reaction activation agent in the form of a toluene solution (Al concentration 9.30 mass %) of the polymethylaluminoxane composition prepared in Preliminary Test 1 in a quantity equivalent to 49.0 mmol (14.23 g in solution) based on aluminum atoms. Subsequently, the mixture was heated for nine hours at 65° C. to obtain a toluene solution of polymethylaluminoxane in which acetophenone was employed as a source of oxygen. The solution obtained was a pale yellow transparent liquid free of gelled material. The results of aluminum analysis conducted following recovery of the reaction solution indicated the quantitative reaction yield based on aluminum atoms. The aluminum concentration of the reaction solution obtained was 9.15 mass %. The quantity of Me(TMAL) in the polymethylaluminoxane composition in solution obtained was determined by $^1$H-NMR to be 23.2 mol %. Since the polymethylaluminoxane composition was in solution form, the solubility measurement given in the test methodology section was precluded. However, the concentration in toluene, determined by calculation from the specific gravity of the solution and the aluminum concentration, was about 3.1 mol/L.

(2) Ethylene Polymerization Evaluation

Polymerization evaluation by the same method as that described in (2)1. of Preliminary Test 1 revealed the polymerization activity to be $65 \times 10^6$ g-PE/mol-Z·atm·hr. The polymer was amorphous and there was pronounced fouling of the polymerization apparatus.

Preliminary Test 7

A 174.63 g quantity of the polymethylaluminoxane composition in solution prepared in Preliminary Test 1 (Al/O=1.40) was concentrated and solidified under a full vacuum at room temperature, yielding a residual component in the form of 54.03 g of concentrated polymethylaluminoxane. Toluene was added to this residual component and the aluminum concentration was adjusted to 8.92 mass %. The toluene solution of polymethylaluminoxane composition obtained was a uniform solution free of insoluble material. The quantity of Me(TMAL) as determined by $^1$H-NMR was 15.0 mol %, which was much lower than the 26.0 mol % prior to concentration.

The concentrated, dried polymethylaluminoxane composition was dissolved in benzene and the molecular weight as measured by the drop in solidification point method was 1,220. Accordingly, the degree of polymerization n of the aluminoxane was determined to be 21.

Preliminary Test 8: Evaluation of the Effect of the Quantity of N-Hexane Introduced Six-fold, 10-fold, and 20-fold quantities of n-hexane, based on the volume of the polymethylaluminoxane solution, were added to the toluene solution (Al/O=1.40) of the polymethylaluminoxane composition prepared in Preliminary Test 1 and the change in the quantity of solid polymethylaluminoxane composition that precipitated was measured. As a result, the quantity of solid polymethylaluminoxane composition that precipitated was constant. The aluminum-based precipitation rate was 22 percent in all cases, and no difference based on the quantity of n-hexane introduced was observed.

Embodiment 1

(1) Synthesis of Solid Polymethylaluminoxane Composition

To a separable flask with an internal volume of 5 L equipped with stirrer was charged 406.5 g (1.361 mol-Al) of the polymethylaluminoxane composition prepared in Preliminary Test 4 (Al/O=1.20) and the solution was heated for 8 hours at 100° C. with stirring. A solid polymethylaluminoxane composition precipitated during heating. The solution was cooled to 30° C. or lower and 3.6 L of n-hexane was added with stirring for washing. The solid polymethylaluminoxane composition was decanted, the supernatant was removed, and a decantation washing operation was conducted twice with 3 L of n-hexane. The solid obtained was dried under reduced pressure at room temperature to obtain a dry solid polymethylaluminoxane composition. The precipitation rate of the dry solid polymethylaluminoxane composition was 96 percent based on aluminum atoms in the polymethylaluminoxane composition in solution employed. The quantity of Me(TMAL) in the solid polymethylaluminoxane composition obtained was measured by $^1$H-NMR at 9.0 mol %.

(2) Analysis of the Solid Polymethylaluminoxane Composition (a) Aluminum Content The aluminum content of the dry solid polymethylaluminoxane composition was measured at 37.3 mass %-Al.

(b) Morphology Evaluation

Figure 2:
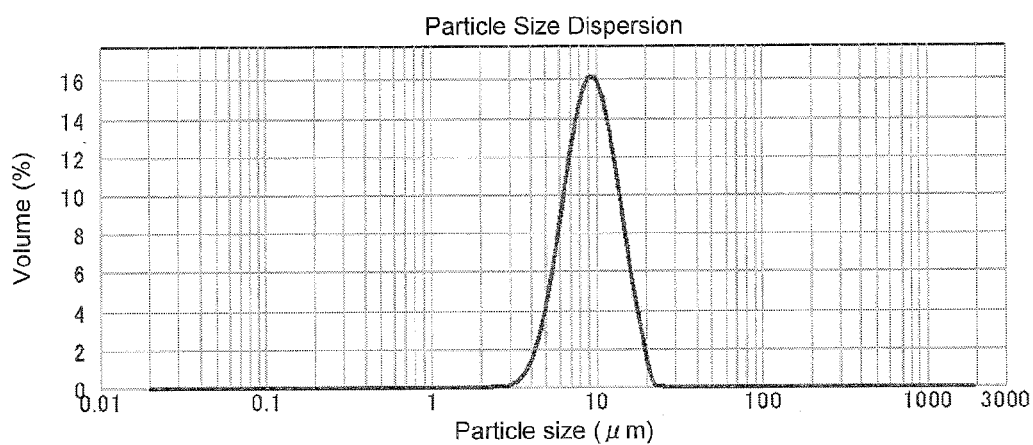
FIG. 2 Results of particle size distribution evaluation by a Master Sizer 2000 Hydro S of the dried solid polymethylaluminoxane composition obtained in Embodiment 1.

Evaluation of the particle size distribution of the dry solid polymethylaluminoxane composition conducted with a Master Sizer 2000 Hydro S revealed a volume-based median diameter d (0.5) of 9.4 µm and a homogeneity of 0.296 (see FIG. 2).

(c) Measurement of Specific Surface Area

Measurement of the specific surface area of the dry solid polymethylaluminoxane composition revealed the specific surface area per mmol of aluminum atoms to be 19.5 m$^2$/mmol-Al.

(d) Solubility in Solvent

The solubility in n-hexane and in toluene of the dry solid polymethylaluminoxane composition was determined to be 0.1 mol % and 0.4 mol %, respectively, which were extremely low values.

(3) Ethylene Polymerization Evaluation

1. Polymerization Employing Bis(Cyclopentadienyl)Dizirconium Dichloride

To a 500 mL four-necked flask equipped with magnetic stirrer was charged 250 mL of toluene. The toluene was heated to 34° C. To this was added a toluene slurry of 0.16 g (5.93 mmol) of the solid polymethylaluminoxane (Al/O=1.20) based on aluminum atoms. Bis(cyclopentadienyl) zirconium dichloride ($Cp_2ZrCl_2$) was added to achieve an Al/Zr mole ratio of 5,000. While raising the temperature to 40° C., ethylene gas was blown in. After 10 minutes, the ethylene gas feed was halted and methanol was introduced to deactivate the catalyst. The polyethylene produced was filtered and dried. The polymerization activity was calculated to be 64×10$^6$ g-PE/mol-Zr·atm·hr.

The polymer obtained was in the form of smooth microparticles that did not adhere to the reaction apparatus following polymerization. The molecular weight was determined to be 160,000 and the Mw/Mn to be 2.7 by high temperature GPC.

2. Polymerization Employing Bis(N-Butylcyclopentadienyl) Zirconium Dichloride

To a 500 mL four-necked flask equipped with magnetic stirrer was charged 250 mL of toluene. The toluene was heated to 34° C. To this was added a toluene solution of 0.038 g (1.4 mmol) of polymethylaluminoxane composition based on aluminum atoms. Bis(n-butylcyclopentadienyl)zirconium dichloride ((nBu-Cp)$_2$ZrCl$_2$) was added to achieve an Al/Zr mole ratio of 5,000. While raising the temperature to 40° C., ethylene gas was blown in. After 10 minutes, the ethylene gas feed was halted and methanol was introduced to deactivate the catalyst. The polyethylene produced was filtered and dried. The polymerization activity was calculated to be 140× 10$^6$ g-PE/mol-Zr·atm·hr. The polymer obtained was in the form of smooth microparticles that did not adhere to the reaction apparatus following polymerization.

3. Polymerization Employing Rac-Ethylenebis(4,5,6-Tetrahydro-1-Indenyl)Zirconium Dichloride To a 500 mL four-necked flask equipped with magnetic stirrer was charged 250 mL of toluene. The toluene was heated to 34° C. To this was added a toluene solution of 0.038 g (1.4 mmol) of polymethylaluminoxane based on aluminum atoms. Rae-ethylene bis(4,5,6-tetrahydro-1-indenyl)zirconium dichloride (rac-Et(Ind)$_2$ZrCl$_2$) was added to achieve an Al/Zr mole ratio of 5,000. While raising the temperature to 40° C., ethylene gas was blown in. After 10 minutes, the ethylene gas feed was halted and methanol was introduced to deactivate the catalyst. The polyethylene produced was filtered and dried. The polymerization activity was calculated to be 51×10$^6$ g-PE/mol-Zr·atm·hr. The polymer obtained was in the form of smooth microparticles that did not adhere to the reaction apparatus following polymerization.

Embodiment 1-2

Figure 3:
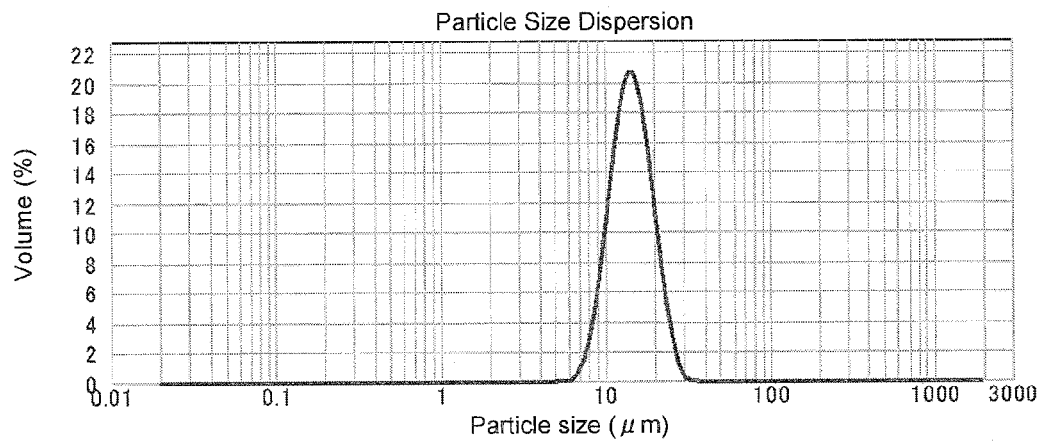
FIG. 3 Results of particle size distribution evaluation by a Master Sizer 2000 Hydro S of the solid polymethylaluminoxane composition in solution obtained in Embodiment 1-2 following heating for 4 hours.
Figure 4:
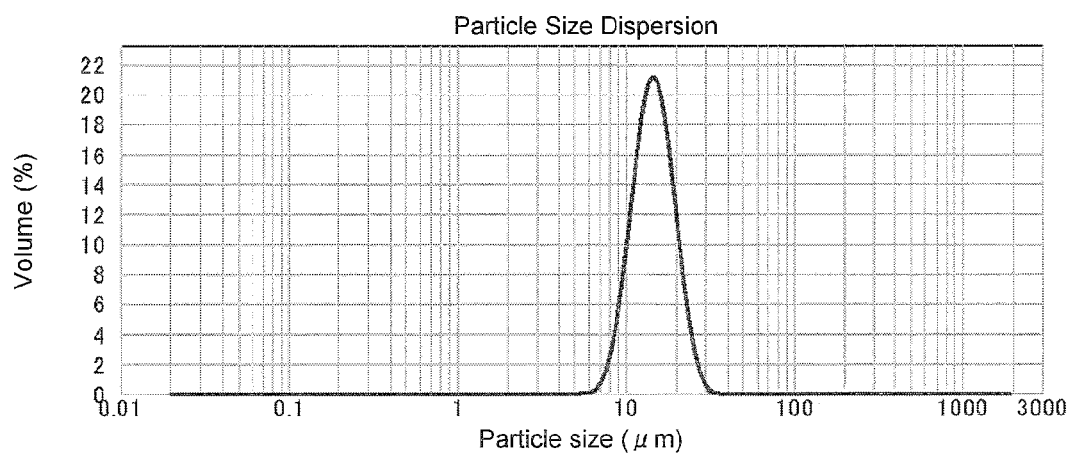
FIG. 4 Results of particle size distribution evaluation by a Master Sizer 2000 Hydro S of the solid polymethylaluminoxane composition in solution obtained in Embodiment 1-2 following heating for 8 hours.

A toluene solution of the polymethylaluminoxane composition prepared in Preliminary Test 4 was heat treated in the same manner as in Embodiment 1 to induce the precipitation of a solid product. Subsequently, without washing with n-hexane, the particle size distribution of the reaction solution was directly measured. Toluene was employed as solvent in a Master Sizer 2,000 Hydro S. As a result, the particle morphology was such that at hour 4 of heating, the median diameter d (0.5) based on volume was 14.5 µm (see FIG. 3) and at hour 8 of heating, the median diameter d (0.5) based on volume was 14.6 µm (see FIG. 4).

In Embodiment 1, the particle size distribution was evaluated for a dry solid polymethylaluminoxane composition, yielding the result of a median diameter d (0.5) based on volume of 9.4 µm and a homogeneity of 0.296. In the present embodiment, evaluation testing of the particle size distribution of a toluene dispersion of the solid polymethylaluminoxane composition was conducted without drying. The median diameter d(0.5) of the particle size distribution exceeded 10 µm. This was attributed to swelling of the solid polymethylaluminoxane composition in the toluene dispersion of the undried solid polymethylaluminoxane composition.

Embodiment 2

(1) Synthesis of Solid Polymethylaluminoxane Composition

With the exception that the polymethylaluminoxane composition in solution (Al/O=1.25) prepared in Preliminary Test 3 was employed, a solid polymethylaluminoxane composition was prepared in the same manner as in Embodiment 1. The precipitation rate of the dry solid was 72 percent based on the aluminum atoms in the polymethylaluminoxane composition in solution employed. The quantity of Me(TMAL) in the solid polymethylaluminoxane composition obtained was measured by $^1$H-NMR at 10.5 mol %.

(2) Analysis of the Solid Polymethylaluminoxane Composition (a) Aluminum Content The aluminum content of the dry solid polymethylaluminoxane composition was measured at 40.3 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 28.3 µm and a homogeneity of 0.339.

(c) Measurement of Specific Surface Area

Measurement of the specific surface area of the dry solid polymethylaluminoxane composition revealed the specific surface area per mmol of aluminum atoms to be 17.6 m$^2$/mmol-Al.

(d) Solubility in Solvent

The solubility in n-hexane and in toluene of the dry solid polymethylaluminoxane composition was determined to be 0.2 mol % and 0.6 mol %, respectively, which were low values.

(3) Ethylene Polymerization Evaluation

With the exception that the solid polymethylaluminoxane composition synthesized above was employed, polymerization evaluation conducted in the same manner as in (3)1. in Embodiment 1 revealed a polymerization activity of 34×10$^6$ g-PE/mol-Zr·atm·hr.

The polymer obtained was in the form of smooth microparticles that did not adhere to the reaction apparatus following polymerization.

Embodiment 3

(1) Synthesis of Solid Polymethylaluminoxane Composition

With the exception that the polymethylaluminoxane composition in solution (Al/O=1.30) prepared in Preliminary Test 2 was employed, a solid polymethylaluminoxane composition was prepared in the same manner as in Embodiment 1. The precipitation rate of the dry solid was 65 percent based on the aluminum atoms in the polymethylaluminoxane composition in solution employed. The quantity of Me(TMAL) in the solid polymethylaluminoxane composition obtained was measured by $^1$H-NMR at 11.5 mol %.

(2) Analysis of the Solid Polymethylaluminoxane Composition (a) Aluminum Content The aluminum content of the dry solid polymethylaluminoxane composition was measured at 38.5 mass %-Al.

(b) Morphology Evaluation

Figure 5:
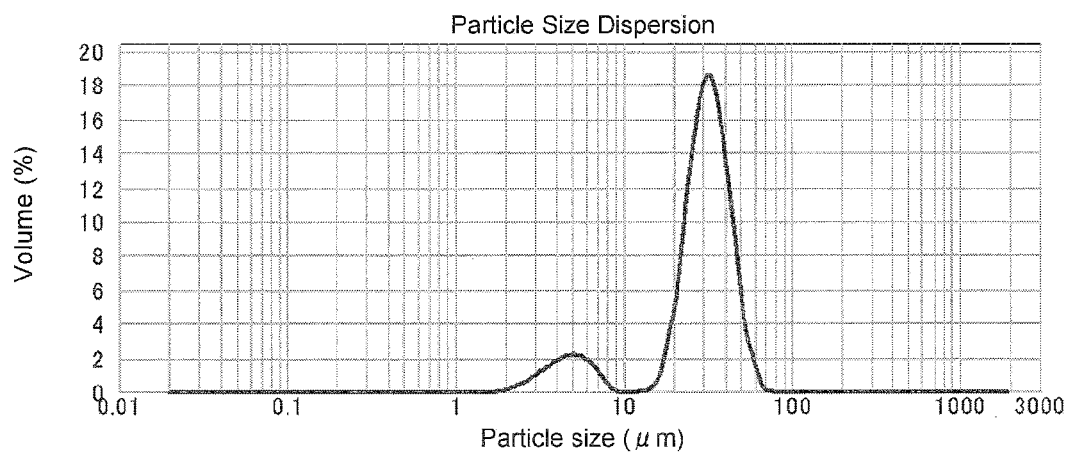
FIG. 5 Results of particle size distribution evaluation by a Master Sizer 2000 Hydro S of the dried solid polymethylaluminoxane composition obtained in Embodiment 3.

Evaluation of the particle size distribution of the dry solid polymethylaluminoxane composition conducted with a Master Sizer 2000 Hydro S revealed a volume-based median diameter d (0.5) of 30.9 μm and a homogeneity of 0.313 (see FIG. 5).

(c) The Solubility in Solvent

The solubility in n-hexane and in toluene of the dry solid polymethylaluminoxane composition was determined to be 0.4 mol % and 1.4 mol %, respectively, which were low values.

(3) Ethylene Polymerization Evaluation

With the exception that the solid polymethylaluminoxane composition synthesized above was employed, polymerization evaluation conducted in the same manner as in (3)1. in Embodiment 1 revealed a polymerization activity of $33 \times 10^6$ g-PE/mol-Zr·atm·hr.

The polymer obtained was in the form of smooth microparticles that did not adhere to the reaction apparatus following polymerization.

Embodiment 4

(1) Synthesis of Solid Polymethylaluminoxane Composition

With the exception that the period of heating the toluene solution of the polymethylaluminoxane composition prepared in Preliminary Test 2 at 100° C. was changed to 16 hours, a solid polymethylaluminoxane composition was prepared in the same manner as in Embodiment 3. The precipitation rate of the dry solid was 75 percent based on the aluminum atoms in the polymethylaluminoxane composition in solution employed. The quantity of Me(TMAL) in the solid polymethylaluminoxane composition obtained was measured by $^1$H-NMR at 11.0 mol %.

(2) Analysis of the Solid Polymethylaluminoxane Composition (a) Aluminum Content The aluminum content of the dry solid polymethylaluminoxane composition was measured at 40.2 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 28.7 μm and a homogeneity of 0.422.

(c) Measurement of Specific Surface Area

Measurement of the specific surface area of the dry solid polymethylaluminoxane composition revealed the specific surface area per mmol of aluminum atoms to be 21.1 $m^2$/mmol-Al.

(d) Solubility in Solvent

The solubility in n-hexane and in toluene of the dry solid polymethylaluminoxane composition was determined to be 0.3 mol % and 1.2 mol %, respectively, which were low values.

(3) Ethylene Polymerization Evaluation

With the exception that the solid polymethylaluminoxane composition synthesized above was employed, polymerization evaluation conducted in the same manner as in (3)1. in Embodiment 1 revealed a polymerization activity of $30 \times 10^6$ g-PE/mol-Zr·atm·hr.

The polymer obtained was in the form of smooth microparticles that did not adhere to the reaction apparatus following polymerization.

Embodiment 5

(1) Synthesis of Solid Polymethylaluminoxane Composition

With the exception that the polymethylaluminoxane composition in solution (Al/O=1.40) prepared in Preliminary Test 1 was employed, a solid polymethylaluminoxane composition was prepared in the same manner as in Embodiment 1. The precipitation rate of the dry solid was 54.6 percent based on the aluminum atoms in the polymethylaluminoxane composition in solution employed. The quantity of Me(TMAL) in the solid polymethylaluminoxane composition obtained was measured by $^1$H-NMR at 11.5 mol %.

(2) Analysis of the Solid Polymethylaluminoxane Composition (a) Aluminum Content The aluminum content of the dry solid polymethylaluminoxane composition was measured at 38.4 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 10.3 μm and a homogeneity of 0.366.

(c) Measurement of Specific Surface Area

Measurement of the specific surface area of the dry solid polymethylaluminoxane composition revealed the specific surface area per mmol of aluminum atoms to be 18.3 $m^2$/mmol-Al.

(d) Solubility in Solvent

The solubility in n-hexane and in toluene of the dry solid polymethylaluminoxane composition was determined to be 0.5 mol % and 1.5 mol %, respectively, which were low values.

(3) Ethylene Polymerization Evaluation

With the exception that the solid polymethylaluminoxane composition synthesized above was employed, polymerization evaluation conducted in the same manner as in (3)1. in Embodiment 1 revealed a polymerization activity of $38 \times 10^6$ g-PE/mol-Zr·atm·hr.

The polymer obtained was in the form of smooth microparticles that did not adhere to the reaction apparatus following polymerization.

Embodiment 6

(1) Synthesis of Solid Polymethylaluminoxane Composition

With the exceptions that the polymethylaluminoxane composition in solution (Al/O=1.40) prepared in Preliminary Test 1 was employed and the period of heating at 100° C. was changed to 16 hours, a solid polymethylaluminoxane composition was prepared in the same manner as in Embodiment 1. The precipitation rate of the dry solid was 62 percent based on the aluminum atoms in the polymethylaluminoxane composition in solution employed. The quantity of Me(TMAL) in the solid polymethylaluminoxane composition obtained was measured by $^1$H-NMR at 12.0 mol %.

(2) Analysis of the Solid Polymethylaluminoxane Composition (a) Aluminum Content The aluminum content of the dry solid polymethylaluminoxane composition was measured at 40.1 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 8.2 μm and a homogeneity of 0.345.

(c) Measurement of Specific Surface Area

Measurement of the specific surface area of the dry solid polymethylaluminoxane composition revealed the specific surface area per mmol of aluminum atoms to be 16.8 $m^2$/mmol-Al.

(3) Ethylene Polymerization Evaluation
1. Polymerization Employing Bis(Cyclopentadienyl)Zirconium Dichloride With the exception that the solid polymethylaluminoxane composition synthesized above was employed, polymerization evaluation conducted in the same manner as in (3)1. in Embodiment 1 revealed polymerization activity of $40 \times 10^6$ g-PE/mol-Zr·atm·hr. The polymer obtained was in the form of smooth microparticles that did not adhere to the reaction apparatus following polymerization.

2. Polymerization Employing Bis(N-Butylcyclopentadienyl) Zirconium Dichloride

With the exception that the solid polymethylaluminoxane composition synthesized above was employed, polymerization evaluation conducted in the same manner as in (3)2. in Embodiment 1 revealed polymerization activity of $135 \times 10^6$ g-PE/mol-Zr·atm·hr. The polymer obtained was in the form of smooth microparticles that did not adhere to the reaction apparatus following polymerization.

Embodiment 7

With the exception that the polymethylaluminoxane composition in solution (Al/O=1.39) prepared in Preliminary Test 6 was employed, a solid polymethylaluminoxane composition was prepared in the same manner as in Embodiment 1. The precipitation rate of the dry solid was 54.8 percent based on the aluminum atoms in the polymethylaluminoxane composition in solution employed. The quantity of Me(TMAL) in the solid polymethylaluminoxane composition obtained was measured by $^1$H-NMR at 11.8 mol %.

(2) Analysis of the Solid Polymethylaluminoxane Composition
(a) Aluminum Content The aluminum content of the dry solid polymethylaluminoxane composition was measured at 40.1 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 6.2 µm and a homogeneity of 0.300.

(c) Measurement of Specific Surface Area

Measurement of the specific surface area of the dry solid polymethylaluminoxane composition revealed the specific surface area per mmol of aluminum atoms to be 13.2 $m^2$/mmol-Al.

(3) Ethylene Polymerization Evaluation

With the exception that the solid polymethylaluminoxane composition synthesized above was employed, polymerization evaluation conducted in the same manner as in (3)1. in Embodiment 1 revealed polymerization activity of $37 \times 10^6$ g-PE/mol-Zr·atm·hr. The polymer obtained was in the form of smooth microparticles that did not adhere to the reaction apparatus following polymerization.

Embodiment 8

The Case of Reducing the Trimethylaluminum Content by Concentration

With the exception that the polymethylaluminoxane composition in solution prepared in Preliminary Test 7 was employed, a solid polymethylaluminoxane composition was prepared in the same manner as in Embodiment 1. The precipitation rate of the dry solid was 70.0 percent based on the aluminum atoms in the polymethylaluminoxane composition in solution employed. The quantity of Me(TMAL) in the solid polymethylaluminoxane composition obtained was measured by $^1$H-NMR at 10.5 mol %.

(2) Analysis of the Solid Polymethylaluminoxane Composition
(a) Aluminum Content The aluminum content of the dry solid polymethylaluminoxane composition was measured at 40.2 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 42.8 µm and a homogeneity of 0.322.

(c) Measurement of Specific Surface Area

Measurement of the specific surface area of the dry solid polymethylaluminoxane composition revealed the specific surface area per mmol of aluminum atoms to be 20.1 $m^2$/mmol-Al.

(3) Ethylene Polymerization Evaluation

With the exception that the solid polymethylaluminoxane composition synthesized above was employed, polymerization evaluation conducted in the same manner as in (3)1. in Embodiment 1 revealed polymerization activity of $33 \times 10^6$ g-PE/mol-Zr·atm·hr. The polymer obtained was in the form of smooth microparticles that did not adhere to the reaction apparatus following polymerization.

Embodiment 9

The Effect of the N-Hexane Addition Period

With the exception that the n-hexane was added over 60 minutes, a solid polymethylaluminoxane composition was prepared in the same manner as in Embodiment 1. The precipitation rate of the dry solid polymethylaluminoxane composition was 97.4 percent based on the aluminum atoms in the polymethylaluminoxane composition in solution employed. The quantity of Me(TMAL) in the solid polymethylaluminoxane composition obtained was measured by $^1$H-NMR at 8.8 mol %.

(2) Analysis of the Solid Polymethylaluminoxane Composition
(a) Aluminum Content The aluminum content of the dry solid polymethylaluminoxane composition was measured at 38.2 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 10.1 µm and a homogeneity of 0.290.

(c) Measurement of Specific Surface Area

Measurement of the specific surface area of the dry solid polymethylaluminoxane composition revealed the specific surface area per mmol of aluminum atoms to be 20.8 $m^2$/mmol-Al.

(d) Solubility in Solvent

The solubility in n-hexane and in toluene of the dry solid polymethylaluminoxane composition was determined to be 0.11 mol % and 0.42 mol %, respectively, which were extremely low values.

(3) Ethylene Polymerization Evaluation

With the exception that the solid polymethylaluminoxane composition synthesized above was employed, polymerization evaluation conducted in the same manner as in (3)1. in Embodiment 1 revealed a polymerization activity of $66 \times 10^6$ g-PE/mol-Zr·atm·hr. The polymer obtained was in the form of smooth microparticles that did not adhere to the reaction apparatus following polymerization.

Embodiment 10

The Effect of the Heating Period

Figure 6:
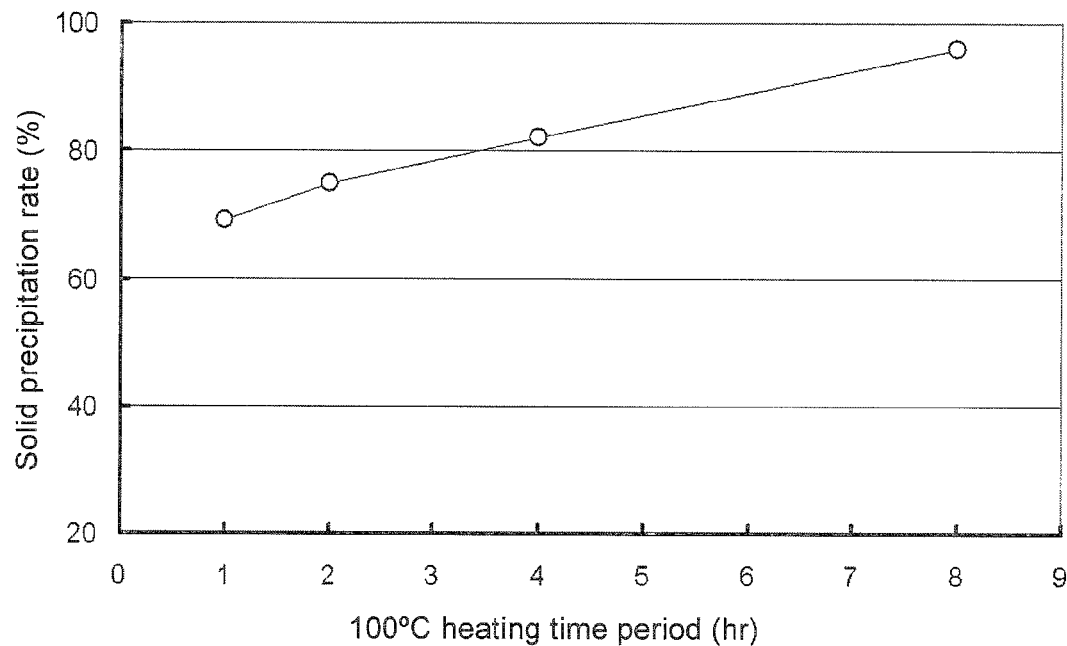
FIG. 6 Results showing the effect of heating time on the precipitation rate of the solid methylaluminoxane composition obtained in Embodiment 10.

The effect of the heating period under the conditions described in Embodiment 1 was examined using the polyethylaluminoxane composition in solution prepared in Preliminary Test 4. The results of measurement of the solid precipitation rate are given in FIG. 6.

Embodiment 11

Processing a Diluted Solution

The polymethylaluminoxane composition prepared in Preliminary Test 4 was diluted with toluene to an aluminum concentration of 4.55 mass %. No change was observed in the diluted solution; it remained a clear solution. With the exception that the diluted solution was employed, a solid polymethylaluminoxane composition was prepared in the same manner as in Embodiment 1. The precipitation rate of the dry solid was 95.3 percent based on the aluminum atoms in the polymethylaluminoxane composition in solution employed. The quantity of Me(TMAL) in the solid polymethylaluminoxane composition obtained was measured by $^1$H-NMR at 9.2 mol %.

(2) Analysis of the Solid Polymethylaluminoxane Composition (a) Aluminum Content The aluminum content of the dry solid polymethylaluminoxane composition was measured at 37.8 mass %-Al.

(b) Morphology Evaluation

Figure 7:
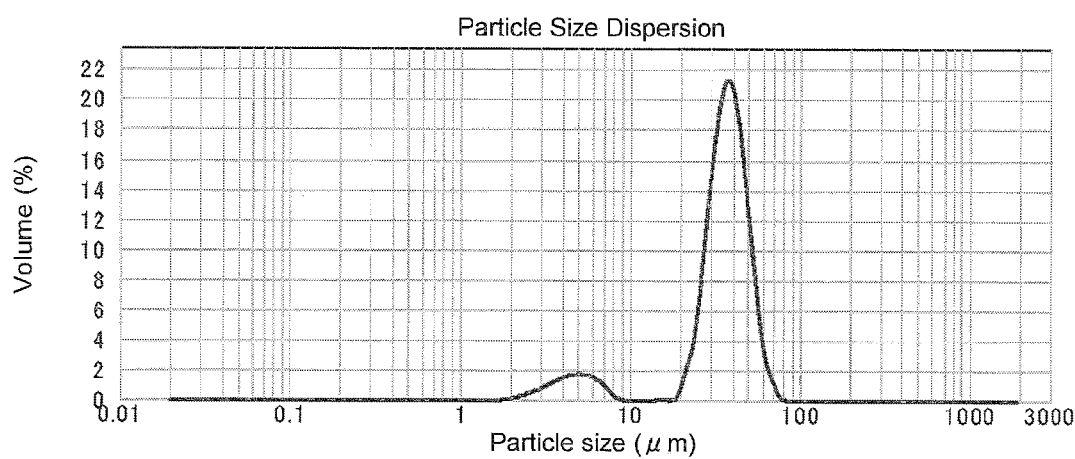
FIG. 7 Results of particle size distribution evaluation by a Master Sizer 2000 Hydro S of the dried, solid polymethylaluminoxane composition obtained in Embodiment 11.

Evaluation of the particle size distribution of the dry solid polymethylaluminoxane composition conducted with a Master Sizer 2000 Hydro S revealed a volume-based median diameter d (0.5) of 36.7 μm and a homogeneity of 0.276 (see FIG. 7).

Comparative Example 1

(1) Synthesis of Solid Polymethylaluminoxane Composition

With the exception that n-hexane was added without conducting a heat treatment, a solid polymethylaluminoxane composition (Al/O=1.40) was synthesized in the same manner as in Embodiment 5. The precipitation rate of the dry solid was 22 percent based on the aluminum atoms in the polymethylaluminoxane composition in solution employed. The quantity of Me(TMAL) in the solid polymethylaluminoxane composition obtained was measured by $^1$H-NMR at 12.5 mol %.

(2) Analysis of the Solid Polymethylaluminoxane Composition (a) Aluminum Content The aluminum content of the dry solid polymethylaluminoxane composition was measured by chelate titration at 37.8 mass %-Al.

(b) Morphology Evaluation

Figure 8:
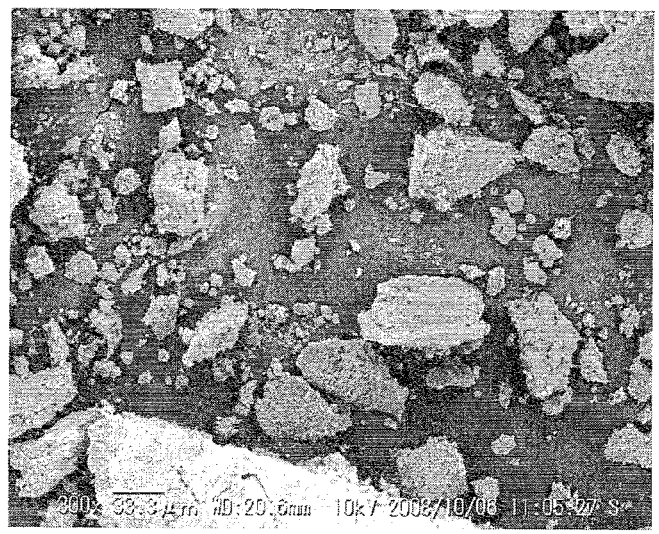
FIG. 8 An electron microscope photograph (300×) of the solid polymethylaluminoxane composition obtained in Comparative Example 1.

Evaluation of the particle size distribution of the dry solid polymethylaluminoxane composition conducted with a Master Sizer 2000 Hydro S revealed a volume-based median diameter d (0.5) of 330.8 μm. Observation by electron microscopy revealed an irregular shape that reflected a complete lack of shape control. FIG. 8 shows the electron microscope photograph that was taken.

(c) Measurement of Specific Surface Area

Measurement of the specific surface area of the dry solid polymethylaluminoxane composition revealed the specific surface area per mmol of aluminum atoms to be 17.0 m$^2$/mmol-Al.

(d) Solubility in Solvent

The solubility in n-hexane and in toluene of the dry solid polymethylaluminoxane composition was determined to be 4.2 mol % and 15.2 mol %, respectively.

(3) Ethylene Polymerization Evaluation

With the exception that the solid polymethylaluminoxane composition synthesized above was employed, polymerization evaluation conducted by the same method as in (3)1. in Embodiment 1 revealed a polymerization activity of 58×10$^6$ g-PE/mol-Zr·atm·hr. The polymer obtained was amorphous, and adhered in large quantity to the reaction vessel following polymerization.

Comparative Example 2

(1) Synthesis of Solid Polymethylaluminoxane Composition

With the exception that n-hexane was added without conducting a heat treatment, a solid polymethylaluminoxane composition (Al/O=1.30) was synthesized in the same manner as in Embodiment 3. The precipitation rate of the dry solid was 31 percent based on the aluminum atoms in the polymethylaluminoxane employed. The quantity of Me(TMAL) in the solid polymethylaluminoxane composition obtained was measured by $^1$H-NMR at 12.2 mol %.

(2) Analysis of the Solid Polymethylaluminoxane Composition (a) Aluminum Content The aluminum content of the dry solid polymethylaluminoxane composition was measured by chelate titration at 36.0 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 590.2 μm. Observation by electron microscopy revealed an irregular shape that reflected a complete lack of shape control similar to FIG. 8 in Comparative Example 1.

(c) Measurement of Specific Surface Area

Measurement of the specific surface area of the dry solid polymethylaluminoxane composition revealed the specific surface area per mmol of aluminum atoms to be 16.7 m$^2$/mmol-Al.

(d) Solubility in Solvent

The solubility in n-hexane and in toluene of the dry solid polymethylaluminoxane composition was determined to be 2.7 mol % and 12.5 mol %, respectively.

(3) Ethylene Polymerization Evaluation

With the exception that the solid polymethylaluminoxane composition synthesized above was employed, polymerization evaluation conducted by the same method as in (3)1. in Embodiment 1 revealed a polymerization activity of 40×10$^6$ g-PE/mol-Zr·atm·hr. The polymer obtained was amorphous, and adhered in large quantity to the reaction vessel following polymerization.

Comparative Example 3

(1) Synthesis of Solid Polymethylaluminoxane Composition

With the exception that n-hexane was added without conducting a heat treatment, a solid polymethylaluminoxane composition (Al/O=1.25) was synthesized in the same manner as in Embodiment 2. The precipitation rate of the dry solid was 34.4 percent based on the aluminum atoms in the polymethylaluminoxane composition in solution employed. The quantity of Me(TMAL) in the solid polymethylaluminoxane composition obtained was measured by $^1$H-NMR at 13.1 mol %.

(2) Analysis of the Solid Polymethylaluminoxane Composition (a) Aluminum Content The aluminum content of the dry solid polymethylaluminoxane composition was measured by chelate titration at 33.6 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 575.2 μm. Observation by electron microscopy revealed an irregular shape that reflected a complete lack of shape control similar to FIG. 8 in Comparative Example 1.

(c) Measurement of Specific Surface Area

Measurement of the specific surface area of the dry solid polymethylaluminoxane composition revealed the specific surface area per mmol of aluminum atoms to be 17.0 m$^2$/mmol-Al.

(3) Ethylene Polymerization Evaluation

With the exception that the solid polymethylaluminoxane composition synthesized above was employed, polymerization evaluation conducted by the same method as in (3)1. in Embodiment 1 revealed a polymerization activity of 29×10$^6$ g-PE/mol-Zr·atm·hr. The polymer obtained was amorphous, and adhered in large quantity to the reaction vessel following polymerization. High temperature GPC analysis of the polymer revealed a molecular weight of 180,000 and a Mw/Mn of 2.6.

Comparative Example 4

(1) Synthesis of Solid Polymethylaluminoxane Composition

With the exception that n-hexane was added without conducting a heat treatment using the polymethylaluminoxane composition in solution prepared in Preliminary Test 4, a solid polymethylaluminoxane composition was synthesized in the same manner as in Embodiment 1. The precipitation rate of the dry solid was 47.0 percent based on the aluminum atoms in the polymethylaluminoxane composition in solution employed. The quantity of Me(TMAL) in the solid polymethylaluminoxane composition obtained was measured by $^1$H-NMR at 11.5 mol %.

(2) Analysis of the Solid Polymethylaluminoxane Composition (a) Aluminum Content The aluminum content of the dry solid polymethylaluminoxane composition was measured by chelate titration at 36.8 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 508.6 μm. Observation by electron microscopy revealed an irregular shape that reflected a complete lack of shape control similar to FIG. 8 in Comparative Example 1.

(c) Measurement of Specific Surface Area

Measurement of the specific surface area of the dry solid polymethylaluminoxane composition revealed the specific surface area per mmol of aluminum atoms to be 17.6 m$^2$/mmol-Al.

(d) Solubility in Solvent

The solubility in n-hexane and in toluene of the dry solid polymethylaluminoxane composition was determined to be 0.8 mol % and 1.6 mol %, respectively.

(3) Ethylene Polymerization Evaluation

With the exception that the solid polymethylaluminoxane composition synthesized above was employed, polymerization evaluation conducted by the same method as in (3)1. in Embodiment 1 revealed a polymerization activity of 30×10$^6$ g-PE/mol-Zr·atm·hr. The polymer obtained was amorphous, and adhered in large quantity to the reaction vessel following polymerization.

Comparative Example 5

(1) Synthesis of Solid Polymethylaluminoxane Composition

With the exception that n-hexane was added without heat treating the polymethylaluminoxane composition in solution prepared in Preliminary Test 7, a solid polymethylaluminoxane composition was synthesized in the same manner as in Embodiment 1. The precipitation rate of the dry solid was 24.5 percent based on the aluminum atoms in the polymethylaluminoxane composition in solution employed. The quantity of Me(TMAL) in the solid polymethylaluminoxane composition obtained was measured by $^1$H-NMR at 12.7 mol %.

(2) Analysis of the Solid Polymethylaluminoxane Composition (a) Aluminum Content The aluminum content of the dry solid polymethylaluminoxane composition was measured by chelate titration at 38.4 mass %-Al.

(b) Morphology Evaluation

Evaluation of the particle size distribution of the dry solid polymethylaluminoxane composition conducted with a Master Sizer 2000 Hydro S revealed a volume-based median diameter d (0.5) of 317 μm. Observation by electron microscopy revealed an irregular shape that reflected a complete lack of shape control similar to FIG. 8 in Comparative Example 1.

(c) Measurement of Specific Surface Area

Measurement of the specific surface area of the dry solid polymethylaluminoxane composition revealed the specific surface area per mmol of aluminum atoms to be 16.5 m$^2$/mmol-Al.

(3) Ethylene Polymerization Evaluation

With the exception that the solid polymethylaluminoxane composition synthesized above was employed, polymerization evaluation conducted by the same method as in (3)1. in Embodiment 1 revealed a polymerization activity of 36×10$^6$ g-PE/mol-Zr·atm·hr. The polymer obtained was amorphous, and adhered in large quantity to the reaction vessel following polymerization.

Comparative Example 6

(1) Synthesis of SiO$_2$-Supported Polymethylaluminoxane Composition

To a 1 L four-necked flask equipped with magnetic stirrer was charged 625 mL of toluene. Next, 49.9 g of SiO$_2$ (SiO$_2$ P-10, made by Fuji Silysia) baked at 400° C. for two hours to achieve a surface hydroxyl group concentration of 1.63 mass % was introduced. While stirring, the temperature of the solution was cooled to 5° C. To this was gradually added over 60 minutes 147.6 g (Al/O=1.40, 0.508 mol-Al) of a toluene solution of the polymethylaluminoxane composition prepared in Preliminary Test 1. The mixture was gradually heated to 65° C. and aged for 60 minutes at that temperature. The supernatant of the reaction solution was removed by decantation and washing was conducted five times with 500 mL of toluene. The slurry of the SiO$_2$-supported polymethylaluminoxane composition was dried under reduced pressure at 60° C., yielding 71.77 g of SiO$_2$-supported polymethylaluminoxane composition in the form of a dry solid.

(2) Analysis (a) Aluminum Content

The aluminum content of the dry SiO$_2$-supported polymethylaluminoxane composition was measured by ICP analysis at 15.3 mass %-Al. Based on this aluminum content, the quantity of aluminum recovered as a solid of the SiO$_2$-supported polymethylaluminoxane composition was 80 percent.

(b) Morphology Evaluation

Figure 9:
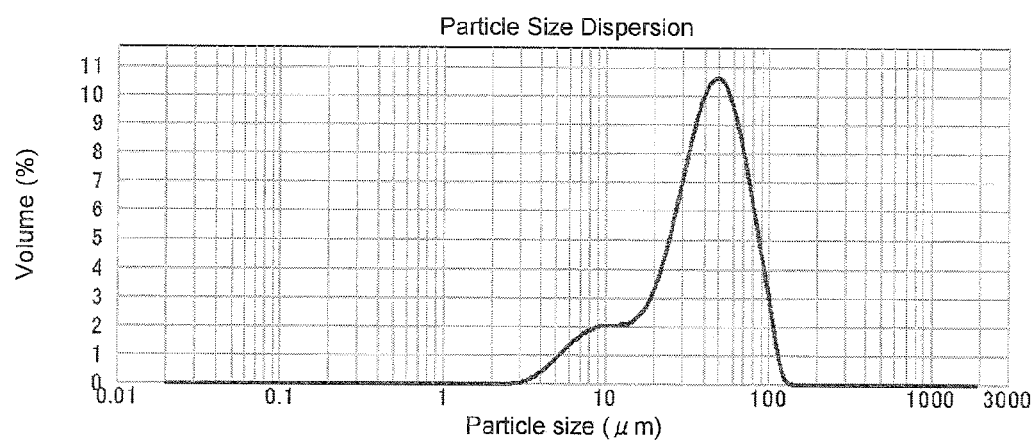
FIG. 9 Results of particle size distribution evaluation by a Master Sizer 2000 Hydro S of the dried, solid polymethylaluminoxane composition obtained in Comparative Example 6.

Evaluation of the particle size distribution of the dry SiO$_2$-supported polymethylaluminoxane composition conducted with a Master Sizer 2000 Hydro S revealed a volume-based median diameter d (0.5) of 41.8 μm and a homogeneity of 0.481 (see FIG. 9).

(c) Measurement of Specific Surface Area

Measurement of the specific surface area of the dry SiO$_2$-supported polymethylaluminoxane composition revealed the specific surface area per mmol of aluminum atoms to be 51.0 m$^2$/mmol-Al.

(3) Ethylene Polymerization Evaluation

With the exception that the dry SiO$_2$-supported polymethylaluminoxane composition synthesized above was employed, polymerization evaluation conducted by the same method as in (3)1. in Embodiment 1 revealed a polymerization activity of 9×10$^6$ g-PE/mol-Zr·atm·hr, which was low activity. The polymer obtained was comprised of microparticles and adhesion to the reaction vessel following polymerization was inhibited. High temperature GPC analysis of the polymer reveled a molecular weight of 160,000 and a Mw/Mn of 3.0.

Comparative Example 7

(1) Synthesis of Dry SiO$_2$-Supported Polymethylaluminoxane Composition

To a 1 L four-necked flask equipped with magnetic stirrer was charged 625 mL of toluene. Next, 49.9 g of SiO$_2$ (SiO$_2$ P-10, made by Fuji Silysia) baked at 400° C. for two hours to achieve a surface hydroxyl group concentration of 1.63 mass % was introduced. While stirring, the temperature of the solution was cooled to 5° C. To this was gradually added over 60 minutes 151.73 g (Al/O=1.20, 0.508 mol-Al) of a toluene solution of the polymethylaluminoxane composition prepared in Preliminary Test 4. The resultant was gradually heated to 65° C. and aged at the same temperature for 60 minutes. As the aging time advanced, the viscosity of the solution increased. The rate of decantation of the SiO$_2$-supported polymethylaluminoxane composition following the conclusion of aging was extremely slow, precluding an operation identical to that in Comparative Example 4. Accordingly, 100 mL of the slurry was collected and toluene was added to conduct washing of the same effectiveness. The slurry of the SiO$_2$-supported polymethylaluminoxane composition obtained was dried under reduced pressure at 60° C., yielding 74.0 g of SiO$_2$-supported polymethylaluminoxane composition in the form of a dry solid.

(2) Analysis of the SiO$_2$-Supported Polymethylaluminoxane Composition (a) Aluminum Content The aluminum content of the dry SiO$_2$-supported polymethylaluminoxane composition was measured by ICP analysis at 16 mass %-Al. Based on this aluminum content, the quantity of aluminum recovered as a solid of the SiO$_2$-supported polymethylaluminoxane composition was 86.3 percent.

(b) Morphology Evaluation

Evaluation of the particle size distribution of the dry SiO$_2$-supported polymethylaluminoxane composition conducted with a Master Sizer 2000 Hydro S revealed a volume-based median diameter d (0.5) of 44.5 μm and a homogeneity of 0.577.

(c) Measurement of Specific Surface Area

Measurement of the specific surface area of the dry SiO$_2$-supported polymethylaluminoxane composition revealed the specific surface area per mmol of aluminum atoms to be 55.1 m$^2$/mmol-Al.

(3) Ethylene Polymerization Evaluation

With the exception that the dry SiO$_2$-supported polymethylaluminoxane composition synthesized above was employed, polymerization evaluation conducted by the same method as in (3)1. in Embodiment 1 revealed a polymerization activity of 17.0×10$^6$ g-PE/mol-Zr·atm·hr. Although greater than the activity of the SiO$_2$-supported polymethylaluminoxane composition described in Comparative Example 6, this activity was still low. The polymer obtained was comprised of microparticles and adhesion to the reaction vessel following polymerization was inhibited.

Comparative Example 8

(1) Synthesis of Solid Polymethylaluminoxane Composition

Corresponding to Patent Reference 16

A solid polymethylaluminoxane composition was synthesized in the same manner as in Embodiment 1 described in Japanese Examined Patent Publication (KOKOKU) Heisei No. 7-42301 using the polymethylaluminoxane composition in solution prepared in Preliminary Test 7. The specific operation will be described below. First, toluene was added to the polymethylaluminoxane composition in solution prepared in Preliminary Test 7 to adjust the aluminum concentration to 4.10 mass %. The weight was 140.0 g in a 500 mL eggplant-shaped flask. While stirring the solution, a 1.5-fold quantity based on volume of dry n-decane was added dropwise over 30 minutes using a dropping funnel. The diluted solution of the polymethylaluminoxane composition began to exhibit turbidity at the point where about 30 mL of n-decane had been added, and had developed a white, turbid state at the end of the dropwise addition. While stirring the diluted solution and reducing the pressure to 4 Torr, the temperature was raised to 35° C. over three hours. The solution was filtered with a glass filter and the liquid phase was removed, yielding a microparticulate polymethylaluminoxane composition. Since the solid obtained was wet and contained n-decane, it was dried for two hours at 60° C. under a full vacuum and then dried for two hours at 100° C. The precipitation rate of the solid was 63.5 percent based on the aluminum atoms of the polymethylaluminoxane composition in solution. The quantity of Me(TMAL) in the solid polymethylaluminoxane composition obtained was measured by $^1$H-NMR at 13.2 mol %.

Figure 10:
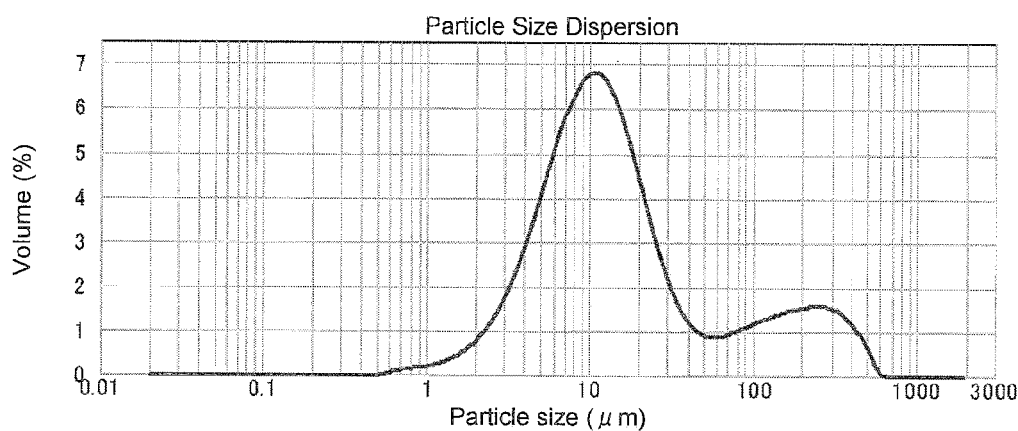
FIG. 10 Results of particle size distribution evaluation by a Master Sizer 2000 Hydro S of the dried, solid polymethylaluminoxane composition obtained in Comparative Example 8.
Figure 11:
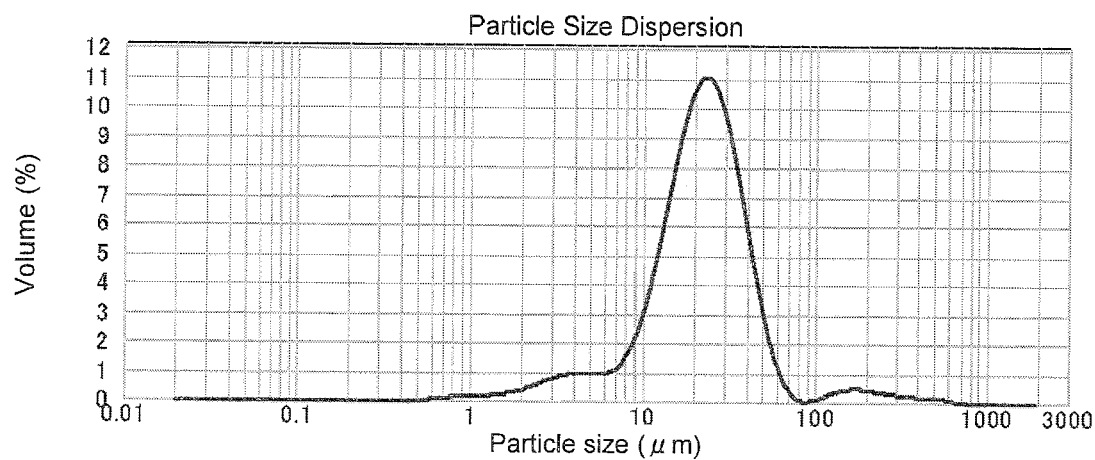
FIG. 11 Results of particle size distribution evaluation by a Master Sizer 2000 Hydro S of the undried, solid polymethylaluminoxane composition obtained in Comparative Example 8.

(2) Analysis of the Solid Polymethylaluminoxane Composition (a) Aluminum Content
The aluminum content of the dry solid polymethylaluminoxane composition was measured by chelate titration at 34.9 mass %-Al.
(b) Morphology Evaluation
Evaluation of the particle size distribution of the dry solid polymethylaluminoxane composition conducted by microtrack revealed a volume-based median diameter d (0.5) of 12.5 μm and a homogeneity of 3.43 (see FIG. 10). Since pulverization might have occurred during drying, the undried product was measured. This revealed a median diameter d (0.5) based on volume of 22.2 μm and a homogeneity of 0.778 (see FIG. 11). This solid polymethylaluminoxane composition was presumed to be relatively brittle.
(c) Measurement of Specific Surface Area
Measurement of the specific surface area of the dry solid polymethylaluminoxane composition revealed the specific surface area per mmol of aluminum atoms to be 18.8 m²/mmol-Al.
(d) Solubility in Solvent
The solubility in n-hexane and in toluene of the dry solid polymethylaluminoxane composition was determined to be 8.3 mol % and 23.6 mol %, respectively.

(3) Ethylene Polymerization Evaluation

With the exception that the solid polymethylaluminoxane composition synthesized above was employed, polymerization evaluation conducted by the same method as in (3)1. in Embodiment 1 revealed a polymerization activity of 34×10⁶ g-PE/mol-Zr·atm·hr. The polymer obtained was amorphous, and in the same manner as in solution polymerization, adhesion of the polymer to the reaction vessel following polymerization was not inhibited.

Comparative Example 9

(1) Synthesis of Solid Polymethylaluminoxane Composition

With the exception that n-hexane was added without heat treating the polymethylaluminoxane composition in solution prepared in Preliminary Test 5, a solid polymethylaluminoxane composition was synthesized in the same manner as in Embodiment 1. The precipitation rate of the dry solid was 63.8 percent based on the aluminum atoms in the polymethylaluminoxane composition in solution employed. The quantity of Me(TMAL) in the solid polymethylaluminoxane composition obtained was measured by $^1$H-NMR at 6.0 mol %.

Figure 12:
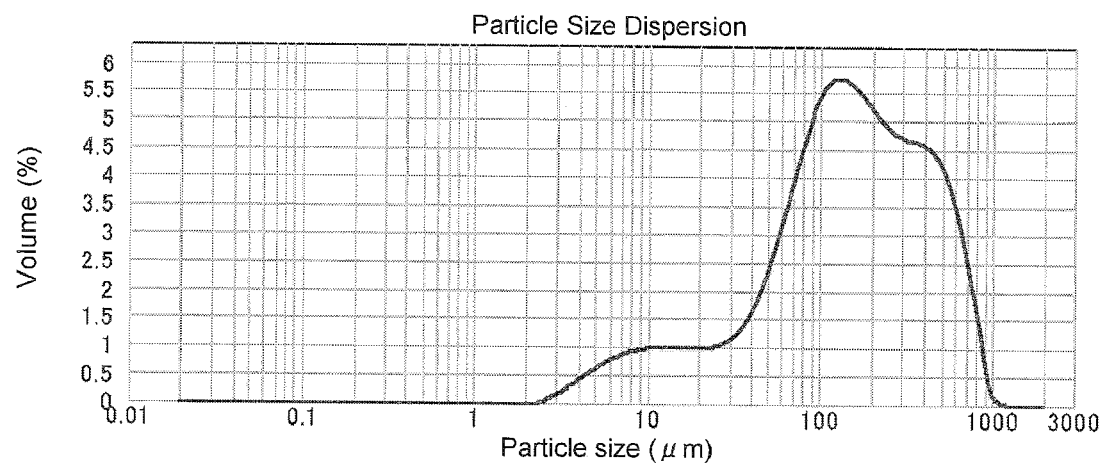
FIG. 12 Results of particle size distribution evaluation by a Master Sizer 2000 Hydro S of the dried, solid polymethylaluminoxane composition obtained in Comparative Example 9.

(2) Analysis of the Solid Polymethylaluminoxane Composition (a) Aluminum Content
The aluminum content of the dry solid polymethylaluminoxane composition was measured by chelate titration at 36.0 mass %-Al.
(b) Morphology Evaluation
Evaluation of the particle size distribution of the dry solid polymethylaluminoxane composition conducted with a Master Sizer 2000 Hydro S revealed a volume-based median diameter d (0.5) of 147.5 μm and a homogeneity of 0.989. However, the particle size distribution was not controlled (see FIG. 12).

INDUSTRIAL APPLICABILITY

The present invention is useful in the area of techniques for manufacturing polyolefins.

The invention claimed is:
1. A solid polymethylaluminoxane composition wherein:
   (i) the aluminum content falls within a range of 36 mass % to 41 mass %;
   (ii) the mole fraction of methyl groups contributed from the trimethylaluminum component relative to the total number of moles of methyl groups is 12 mol % or lower.
2. The composition according to claim 1, having a particulate form with a volume-based median diameter falling within a range of 5 to 50 μm.
3. The composition according to claim 1, having a solubility in n-hexane at 25° C. of 0 to 2 mol %, and having a solubility in toluene at 25° C. of 0 to 2 mol %.
4. The composition according to claim 1, wherein the homogeneity denoted by the following equation is 0.45 or lower:

$$\text{Homogeneity} = \Sigma Xi |d(0.5) - Di| / d(0.5) \Sigma Xi$$

wherein Xi denotes a volume percent of a particle i of the solid polymethylaluminoxane composition shown in a histogram of particle distribution, d(0.5) denotes the median diameter based on volume in the histogram, and Di denotes the diameter based on volume of particle i in the histogram.
5. The composition according to claim 1, having a specific surface area falling within a range of 10 to 25 m²/mmol-Al.

6. The composition according to claim 1, comprising polymethylaluminoxane containing the unit denoted by general formula (I) below and trimethylaluminum:

$$-[(Me)AlO]_n- \qquad (I)$$

wherein n denotes an integer of from 10 to 50.

7. The composition according to claim 1, containing no $SiO_2$.

8. A method for manufacturing the solid polymethylaluminoxane composition described in claim 1, comprising the step of:
(a) heating an aromatic hydrocarbon solution containing polymethylaluminoxane containing the unit denoted by general formula (II) below and trimethylaluminum (referred to as the "polymethylaluminoxane composition in solution" hereinafter) to precipitate a solid polymethylaluminoxane composition containing polymethylaluminoxane and trimethylaluminum:

$$-[(Me)AlO]_n- \qquad (II)$$

wherein n denotes an integer of from 1 to 50.

9. The manufacturing method according to claim 8, wherein the polymethylaluminoxane composition in solution prior to heating exhibits 15 mol% or less of a mole fraction of methyl groups from the trimethylaluminum component relative to the total number of moles of methyl groups.

10. The manufacturing method according to claim 8 wherein in step
(a), a heating temperature and a heating time suited to precipitating the solid polymethylaluminoxane composition are selected from:
(i) a heating temperature ranging from 80 to 200° C.; and
(ii) a heating time of 5 minutes or more but less than 24 hours.

11. The manufacturing method according to claim 8, wherein the polymethylaluminoxane composition in solution that is employed as a starting material in step (a) is obtained by thermally decomposing an alkylaluminum compound having an aluminum-oxygen-carbon bond.

12. The manufacturing method according to claim 11, wherein the alkyl aluminum compound having an aluminum-oxygen-carbon bond is prepared by reacting trimethylaluminum and an oxygen-containing organic compound.

13. The manufacturing method according to claim 12, wherein the oxygen-containing organic compound is the aliphatic or aromatic carboxylic acid denoted by general formula (III):

$$R^1-(COOH)_n \qquad (III)$$

wherein $R^1$ denotes a hydrocarbon group in the form of a C1 to C20 linear or branched alkyl group, alkenyl group, or aryl group, and n denotes an integer of 1 to 5.

14. An olefin polymerization catalyst containing catalytic components in the form of the solid polymethylaluminoxane composition according to claim 1 and a transition metal compound denoted by general formula (IV) below:

$$MR^5R^6R^7R^8 \qquad (IV)$$

wherein M denotes a transition metal element, and one or two of the $R^5$ through $R^8$ organic groups denote a cycloalkadienyl skeleton, and the remainder of the $R^5$ through $R^8$ organic groups independently denote a hydrocarbon group with 1 to 20 carbon atoms, an alkoxy group, an aryloxy group, an alkylsilyl group, an alkylamide group, an alkylimide group, an alkylamino group, an alkylimino group, or a halogen atom.

15. A method for manufacturing a polyolefin, comprising polymerizing an olefin using the catalyst according to claim 14.

16. The olefin polymerization catalyst according to claim 14, wherein the cycloalkadienyl skeleton is selected from a cyclopentadienyl group, a methylcyclopentadienyl group, an ethylcyclopentadienyl group, a butylcyclopentadienyl group, a dimethylcyclopentadienyl group, a pentamethylcyclopentadienyl group; an indenyl group; or a fluorenyl group.

17. The olefin polymerization catalyst according to claim 14, wherein the hydrocarbon group with 1 to 20 carbon atoms is an alkyl group, a cycloalkyl group, an aryl group, or an aralkyl group.

\* \* \* \* \*